(12) United States Patent
Hodge et al.

(10) Patent No.: US 8,603,453 B2
(45) Date of Patent: Dec. 10, 2013

(54) ANTIMICROBIAL POLYMERIC BIGUANIDE AND ACIDIC CO-POLYMER COMPOSITION AND METHOD OF USE

(75) Inventors: David John Hodge, Moreton-on-Lugg (GB); David Alan Pears, Poynton (GB); John Jeffrey Gerrard, Chester (GB); Paula Louise McGeechan, Bury (GB)

(73) Assignee: Arch UK Biocides Limited, Blackley, Manchester (GB)

( * ) Notice: Subject to any disclaimer, the term of this patent is extended or adjusted under 35 U.S.C. 154(b) by 1194 days.

(21) Appl. No.: 10/850,068

(22) Filed: May 20, 2004

(65) Prior Publication Data

US 2005/0013794 A1    Jan. 20, 2005

Related U.S. Application Data

(60) Provisional application No. 60/471,738, filed on May 20, 2003.

(51) Int. Cl.
*A61K 31/79*    (2006.01)

(52) U.S. Cl.
USPC .................................................. 424/78.27

(58) Field of Classification Search
USPC ............ 424/409, 78.27, 78.08; 524/514, 457, 524/237, 195; 525/293, 63
See application file for complete search history.

(56) References Cited

U.S. PATENT DOCUMENTS

| | | | |
|---|---|---|---|
| 4,963,347 A | 10/1990 | Humphries | |
| 5,004,631 A | 4/1991 | Humphries | |
| 5,296,215 A * | 3/1994 | Burke et al. | 424/49 |
| 5,648,167 A | 7/1997 | Peck | |
| 5,993,840 A | 11/1999 | Fawkes et al. | |
| 6,136,885 A | 10/2000 | Rusin et al. | |
| 6,465,412 B1 * | 10/2002 | Mahieu et al. | 510/422 |
| 7,056,533 B2 | 6/2006 | Chudzik et al. | |
| 2003/0187095 A1 | 10/2003 | Cornish et al. | |
| 2003/0224030 A1 * | 12/2003 | Uchiyama et al. | 424/405 |
| 2004/0013638 A1 | 1/2004 | Aubay et al. | |

FOREIGN PATENT DOCUMENTS

| | | |
|---|---|---|
| EP | 0182523 | 5/1986 |
| EP | 0232006 | 8/1987 |
| GB | 2213721 | 8/1989 |
| GB | 2349644 | 11/2000 |
| JP | 61152605 | 7/1986 |
| JP | 61258079 A | 11/1986 |
| JP | 01-117802 A | 5/1989 |
| JP | 03039310 A | 2/1991 |
| JP | 2000 178595 * | 6/2000 |
| WO | 00/02449 | 1/2000 |
| WO | WO 02/28952 A1 * | 4/2002 |
| WO | 03/028766 | 4/2003 |

OTHER PUBLICATIONS

Derwent Summary, Accession No. 2000-574259.*
Fundueanu et al (Int J Pharmaceut 218:13-25, 2001).*
"Principals of Polymerisation," G. Odian, Wiley, Interscience, 3$^{rd}$ Ed., 1991, pp. 303-355.
P. Silley et al., "Impedance microbiology—a rapid change for microbiologists," Journal of Applied Biotechnology, vol. 80, 1996, pp. 233-243.

* cited by examiner

*Primary Examiner* — Craig Ricci
(74) *Attorney, Agent, or Firm* — Dority & Manning, P.A.

(57) ABSTRACT

A composition comprising:
(i) an anti-microbial agent; and
(ii) an acidic co-polymer of the Formula (1)

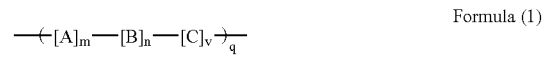

Formula (1)

wherein:
[A] is of Formula (9),

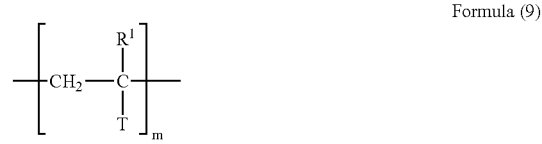

Formula (9)

[B] is of Formula (10),

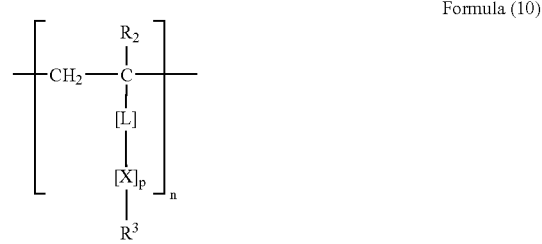

Formula (10)

and [C] is of Formula (12),

Formula (12)

wherein:

[X] is of Formula (11),

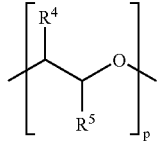

Formula (11)

wherein [A], [B] and [C] may occur in any order;

T is an optionally substituted substituent;

L and G each independently is an optionally substituted linking group;

$R^1$, $R^2$ and $R^3$ are each independently H, optionally substituted $C_{1-20}$-alkyl or optionally substituted $C_{3-20}$-cycloalkyl;

$R^4$ and $R^5$ are each independently H or $C_{1-4}$-alkyl;

q is 15 to 1000;

p is 3 to 50;

J is an optionally substituted hydrocarbyl, group;

F is an acidic substituent;

b is 0, 1, or 2;

m is 0 to 350;

n is 1 to 75;

v is 1 to 100; and w is 1 to 4;

provided that at least one of $R^4$ and $R^5$ is H and provided that $R^1$, $R^2$, $R^3$, T, L, J and G do not contain a basic group; and wherein the pka value of the acidic substituent F on the monomer from which [C] is derived is less than 5.5.

15 Claims, 4 Drawing Sheets

ANTIMICROBIAL POLYMERIC BIGUANIDE AND ACIDIC CO-POLYMER COMPOSITION AND METHOD OF USE

CROSS-REFERENCE TO RELATED CASES

Priority is herewith claimed under 35 U.S.C. §119(e) from U.S. Provisional Patent Application No. 60/471,738, filed May 20, 2003, entitled "COMPOSITION AND USE", by David John Hodge et al. The disclosure of this U.S. Provisional Application is incorporated by reference herein in its entirety.

BACKGROUND OF THE INVENTION

1. Field of the Invention

The present invention relates to a method for inhibiting the growth of micro-organisms on surfaces by means of a composition comprising an acidic vinyl comb type co-polymer and an antimicrobial agent. The anti-microbial agent is controllably released from the acidic co-polymer over time thereby providing effective anti-microbial control.

Micro-organisms can be found on many inanimate and animate surfaces. The presence of such micro-organisms can result in unhygienic conditions in hospitals and medical environments, kitchens, bathrooms, toilets and in the preparation and packaging of foodstuffs leading to health risks and contamination.

Several anti-microbial agents exist which are effective against many of the virulent forms of micro-organisms found in the food and health-care environments. Unfortunately, the activity of such agents is insufficient in terms of providing a sustained, surface hygienic effect. This may be due to the high water solubility and/or the lack of substantivity of the anti-microbial agent on a surface which means that the anti-microbial agent is readily displaced. There is therefore a requirement for an anti-microbial agent or an anti-microbial agent in combination with a delivery system which provides a high degree of anti-microbial kill over a sustained period of time.

2. Brief Description of Art

The literature describes various cases where micro-organisms and in particular bacterial fouling may cause damage or lead to contamination of surfaces including for example swimming pools, industrial pipes, architectural structures, ships hulls, hospital theatres, teeth and kitchen surfaces. Indeed, there have been many attempts and approaches to overcome the micro-biological problems associated especially with bacterial growth on inanimate and animate surfaces.

European Patent 0182523 describes how certain polymeric compositions are effective at preventing oral bacteria from colonisation on the surface of teeth. In UK Patent 2213721, an anti-staining composition comprising polymers with anti-bacterial agents were shown to be effective against bacteria found in an oral environment.

In European Patent 0232006, coating compositions comprising sulphonated polymers and a microbiocide for use in marine environments were shown to have hydrolytic instability. In the above cases the coating of a polymer in an aqueous environment with or without microbiocide was substantially erodable, thereby acting by means of a self-polishing effect, thereby reducing the ability of bacteria to colonise on the surface to be protected.

WO00/02449 describes a process for the biocidal treatment of textiles and surfaces comprising high molecular weight grafted co-polymers.

However, none of the above documents describe an antimicrobial system which has the ability to eliminate microorganisms effectively and has a sustained, surface hygienic effect.

The term 'sustained' used hereinafter refers to an antimicrobial agent which is still active even after the surface to which the agent has been applied has been cleansed for example by wiping, rinsing or washing the surface.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
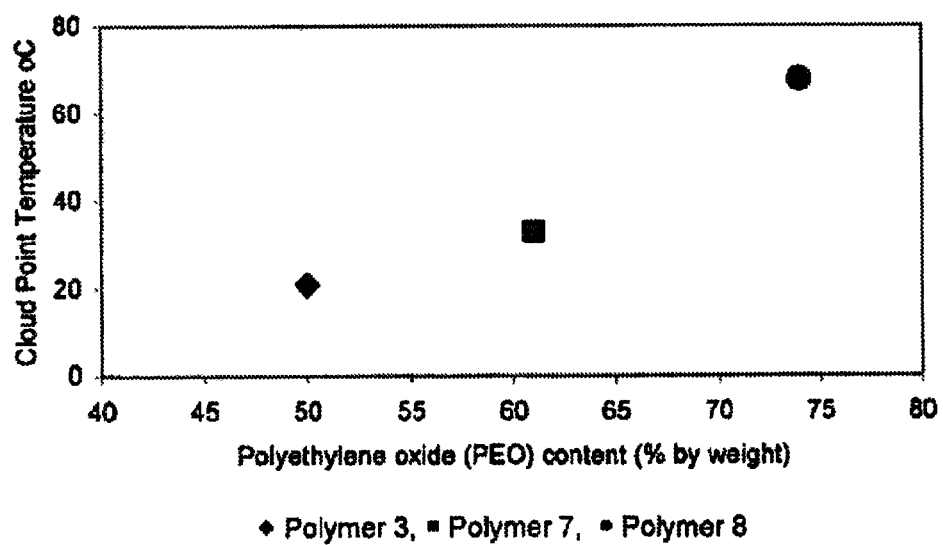
FIG. 1 illustrates the polymer cloud point variation as a function of PEO content and PEO chain length.

Repeat use of reference characters in the present specification and drawings is intended to represent the same or analogous features or elements of the present invention.

DESCRIPTION OF THE INVENTION

Surprisingly, we have now found that a combination of certain anti-microbial agents and acidic vinyl comb type co-polymers (referred to hereinafter as acidic co-polymers) provides effective and sustained anti-microbial activity when used to inhibit the growth of micro-organisms on surfaces. The present invention therefore provides compositions for the treatment of surfaces based on acidic co-polymers with varying functionality in both the backbone and the side chain in combination with an anti-microbial agent, especially a biocide.

Consequently, according to a first aspect of the present invention there is provided a composition comprising:

(i) an anti-microbial agent comprising a polymeric biguanide, alone or in combination with at least one other microbiologically active component selected from the group consisting of quaternary ammonium compounds, monoquaternary heterocyclic amine salts, urea derivatives, amino compounds, imidazole derivatives, nitrile compounds, tin compounds or complexes, isothiazolin-3-ones, thiazole derivatives, nitro compounds, iodine compounds, aldehyde release agents, thiones, triazine derivatives, oxazolidine and derivatives thereof, furan and derivatives thereof, carboxylic acids and the salts and esters thereof, phenol and derivatives thereof, sulphone derivatives, imides, thioamides, 2-mercapto-pyridine-N-oxide, azole fungicides, strobilurins, amides, carbamates, pyridine derivatives, compounds with active halogen groups, and organometallic compounds; and (ii) an acidic co-polymer of the Formula (1):

Formula (1)

wherein:
[A] is of Formula (9),

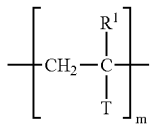

Formula (9)

[B] is of Formula (10),

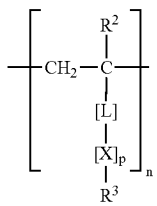

Formula (10)

and [C] is of Formula (12),

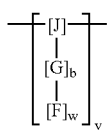

Formula (12)

wherein:
X is of Formula (11),

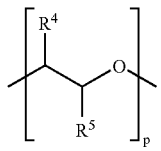

Formula (11)

wherein [A], [B] and [C] may occur in any order;
T is an optionally substituted substituent;
L and G each independently is an optionally substituted linking group;
$R^1$, $R^2$ and $R^3$ are each independently H, optionally substituted $C_{1-20}$-alkyl or optionally substituted $C_{3-20}$-cycloalkyl;
$R^4$ and $R^5$ are each independently H or $C_{1-4}$-alkyl;
q is 15 to 1000;
p is 3 to 50;
J is an optionally substituted hydrocarbyl, group;
F is an acidic substituent;
b is 0, 1, or 2;
m is 0 to 350;
n is 1 to 75;
v is 1 to 100; and
w is 1 to 4;
provided that at least one of $R^4$ and $R^5$ is H and provided that $R^1$, $R^2$, $R^3$, T, L, J and G do not contain a basic group; and
wherein the pka value of the acidic substituent F on the monomer from which [C] is derived is less than 5.5.

A preferred anti-microbial agent for use in the composition according to the first aspect of the present invention is an anti-bacterial agent, more preferably a polymeric biguanide.

Polymeric Biguanide

Preferably the polymeric biguanide comprises at least two biguanide units of Formula (2):

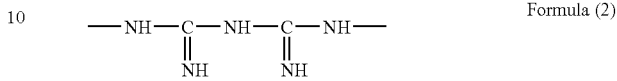

Formula (2)

linked by a bridging group which contains at least one methylene group. The bridging group preferably includes a polymethylene chain, optionally incorporating or substituted by one or more hetero atoms such as oxygen, sulphur or nitrogen. The bridging group may include one or more cyclic moieties which may be saturated or unsaturated. Preferably, the bridging group is such that there are at least three, and especially at least four, carbon atoms directly interposed between two adjacent biguanide units of Formula (2). Preferably, there are not greater than ten and especially not greater than eight carbon atoms interposed between two adjacent biguanide units of Formula (2).

The polymeric biguanide may be terminated by any suitable group, such as a hydrocarbyl, substituted hydrocarbyl or an amine group or a cyanoguanidine group of the Formula (3):

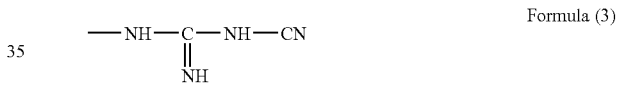

Formula (3)

When the terminating group is hydrocarbyl, it is preferably alkyl, cycloalkyl, aryl or aralkyl. When the hydrocarbyl group is alkyl it may be linear or branched but is preferably linear.

Preferred alkyl groups include $C_{1-8}$-alkyl. Examples of preferred alkyl groups include for example methyl, ethyl, n-propyl, isopropyl, n-pentyl, n-butyl, isobutyl, tert-butyl and n-octyl.

When the hydrocarbyl group is cycloalkyl, it is preferably cyclopropyl, cyclopentyl or cyclohexyl. When the hydrocarbyl group is aralkyl, it preferably contains from 1 to 6, more preferably 1 or 2 carbon atoms in the alkylene group attaching the aryl group to the biguanide. Preferred aralkyl groups include benzyl and 2-phenylethyl groups.

Preferred aryl groups include phenyl groups. When the terminating group is substituted hydrocarbyl, the substituent may be any substituent that does not exhibit undesirable adverse effects on the microbiological properties of the polymeric biguanide. Examples of such substituents are aryloxy, alkoxy, acyl, acyloxy, halogen and nitrile.

When the polymeric biguanide contains two biguanide groups of Formula (2) the biguanide is a bisbiguanide. The two biguanide groups are preferably linked through a polymethylene group, especially a hexamethylene group.

The polymeric biguanide preferably contains more than two biguanide units of Formula (1) and is preferably a linear polymeric biguanide which has a recurring polymeric chain represented by Formula (4) or a salt thereof:

$$\text{—d—NH—}\underset{\underset{NH}{\|}}{C}\text{—NH—}\underset{\underset{NH}{\|}}{C}\text{—NH—e—NH—}\underset{\underset{NH}{\|}}{C}\text{—NH—}\underset{\underset{NH}{\|}}{C}\text{—NH—}$$

Formula (4)

wherein d and e represent bridging groups which may be the same or different and in which together the total of the number of carbon atoms directly interposed between the pairs of nitrogen atoms linked by d plus the number of carbon atoms directly interposed between the pairs of nitrogen atoms linked by e is more than 9 and less than 17.

The bridging groups d and e preferably consist of polymethylene chains, optionally interrupted by hetero atoms, for example, oxygen, sulphur or nitrogen. d and e may also incorporate moieties which may be saturated or unsaturated, in which case the number of carbon atoms directly interposed between the pairs of nitrogen atoms linked by d and e is taken as including that segment of the cyclic group, or groups, which is the shortest. Thus, the number of carbon atoms directly interposed between the nitrogen atoms in the group —NH—CH$_2$—O—[cyclohexane]—O—CH$_2$—NH— is 4 and not 8.

The linear polymeric biguanides having a recurring polymer unit of Formula (4) are typically obtained as mixtures of polymers in which the polymer chains are of different lengths. Preferably, the number of individual biguanide units of Formulae (5a) and (5b):

$$\text{—d—NH—}\underset{\underset{NH}{\|}}{C}\text{—NH—}\underset{\underset{NH}{\|}}{C}\text{—NH—}\text{ and}$$

Formula (5a)

$$\text{—e—NH—}\underset{\underset{NH}{\|}}{C}\text{—NH—}\underset{\underset{NH}{\|}}{C}\text{—NH—}$$

Formula (5b)

is, together, from 3 to about 80.

The preferred linear polymeric biguanide is a mixture of polymer chains in which d and e are identical and the individual polymer chains, excluding the terminating groups, are of the Formula (6) or a salt thereof:

$$\text{—[(CH}_2\text{)}_6\text{—NH—}\underset{\underset{NH}{\|}}{C}\text{—NH—}\underset{\underset{NH}{\|}}{C}\text{—NH]}_{n^1}\text{—}$$

Formula (6)

wherein $n^1$ is from 4 to 20 and especially from 4 to 18. It is especially preferred that the average value of $n^1$ is about 16. Preferably, the average molecular weight of the polymer in the free base form is from 1100 to 4000.

The linear polymeric biguanides may be prepared by the reaction of a bisdicyandiamide having the Formula (7):

$$\text{CN—NH—}\underset{\underset{NH}{\|}}{C}\text{—NH—d—NH—}\underset{\underset{NH}{\|}}{C}\text{—NH—CN}$$

Formula (7)

with a diamine H$_2$N-e-NH$_2$, wherein d and e have the meanings defined above, or, by the reaction between a diamine salt of dicyanamide having the Formula (8):

$$(H_3\overset{+}{N}\text{—}d\text{—}\overset{+}{N}H_3)(\bar{N}(CN)_2)_2$$

Formula (8)

with a diamine H$_2$N-e-NH$_2$ wherein d and e have the meanings defined above. These methods of preparation are described in UK specifications numbers 702,268 and 1,152, 243 respectively, and any of the polymeric biguanides described therein may be used in the present invention.

As noted hereinbefore, the polymer chains of the linear polymeric biguanides may be terminated either by an amino group or by a cyanoguanidine group of Formula (9):

$$\text{—NH—}\underset{\underset{NH}{\|}}{C}\text{—NH—CN}$$

Formula (9)

This cyanoguanidine group can hydrolyse during preparation of the linear polymeric biguanide yielding a guanidine end group. The terminating groups may be the same or different on each polymer chain.

A small proportion of a primary amine R—NH$_2$, where R represents an alkyl group containing from 1 to 18 carbon atoms, may be included with the diamine H$_2$N-e-NH$_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used.

The polymeric biguanides readily form salts with both inorganic and organic acids. Preferred salts of the polymeric biguanide are water-soluble.

It is especially preferred that the polymeric biguanide used in accordance with the present invention is a mixture of linear polymers, the individual polymer chains of which, excluding the terminating groups, are represented by Formula (6) in the hydrochloride salt form. This poly(hexamethylenebiguanide) compound is commercially available from Avecia Limited under the trademarks Vantocil™, Cosmocil™ and Reputex™.

Acidic Co-Polymers

Preferably the acidic co-polymers of the present are as illustrated in the following Empirical Structural Formula.

Empirical Structural Formula

[Diagram showing BACKBONE with SIDE CHAINS]

The term acidic co-polymer referred to herein is used to describe a co-polymer which can be derived from an addition polymerisation reaction (that is, a free radical initiated process which can be carried out in either an aqueous or non aqueous medium) of two or more olefinically unsaturated monomers. Therefore, the term vinyl monomer used throughout refers to an olefinically unsaturated monomer.

Examples of vinyl monomers which may be used to form the acidic co-polymers for use in the present invention include but are not limited to styrene, α-methyl styrene, benzyl methacrylate, acrylonitrile, methacrylonitrile, vinyl halides such as vinyl chloride, vinylidene halides such as vinylidene chloride, vinyl polyethers of ethylene or propylene oxide such as hydroxypolyethoxy (5) polypropoxy (5) monoallyl ether (BX-AA-E5P5 available from Bimax Chemicals Ltd), acrylic acid, methacrylic acid, itaconic acid, maleic acid, fumaric acid, crotonic acid, maleic anhydride and their half esters, and the half esters of phthalic anhydride and hydroxy functional alkyl (meth)acrylates and β-carboxy ethyl acrylate (available from Bimax Chemicals Ltd), 4-styrene carboxylic acid, 3-acrylamido-3-methyl-butanoic acid, 10-acrylamido-undecanoic acid and vinyl benzoic acid. Sulphonic, phosphonic or phosphoric acid-bearing monomers are also suitable, for example 4-styrene sulphonic acid (or the corresponding 4-styrene sulphonyl chloride). Acid bearing monomers can be polymerised as the free acid or as a salt, for example, the ammonium or alkali metal salts of ethylmethacrylate-2-sulphonic acid (available from Laporte as Bisomer SEM), sodium 1-allyloxy-2-hydroxy propane sulphonate, 2-acrylamido-2-methylpropane sulphonic acid, sodium acrylate or the corresponding free acids. Vinyl esters such as vinyl acetate, vinyl propionate, vinyl laurate, and the vinyl esters of versatic acid (available from Resolution Performance Products under the tradename VeoVa), vinyl ethers of heterocyclic vinyl compounds, alkyl esters of mono-olefinically unsaturated dicarboxylic acids (such as di-n-butyl maleate and di-n-butyl fumarate) and in particular, esters of acrylic acid and methacrylic acid, vinyl monomers with additional functionality for subsequent crosslinking of the films, such as diacetone acrylamide, glycidyl methacrylate, aceto acetoxy ethyl methacrylate, hydroxy ethyl acrylate and 2-(trimethylsiloxy)ethyl methacrylate may also be used.

A particularly preferred acidic co-polymer of the present invention is an acrylic co-polymer, derived from acrylic or methacrylic monomers in the form of esters, free acids or salts of the free acids.

The acidic co-polymers of the present invention comprise at least one polymer which comprises one or more repeating units of Formula (1):

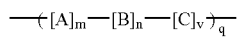

Formula (1)

wherein:
[A] is of Formula (9),

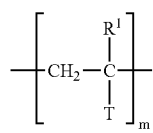

Formula (9)

[B] is of Formula (10),

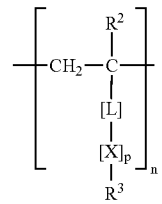

Formula (10)

and [C] is of Formula (12),

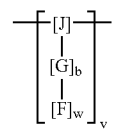

Formula (12)

wherein:
X is of Formula (11)

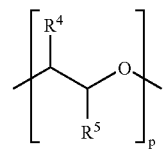

Formula (11)

wherein [A], [B] and [C] may occur in any order;
T is an optionally substituted substituent;
L and G each independently is an optionally substituted linking group;
$R^1$, $R^2$ and $R^3$ are each independently H, optionally substituted $C_{1-20}$-alkyl or optionally substituted $C_{3-20}$-cycloalkyl;
$R^4$ and $R^5$ are each independently H or $C_{1-4}$-alkyl;
q is 15 to 1000;
p is 3 to 50;
J is an optionally substituted hydrocarbyl, group;
F is an acidic substituent;
b is 0, 1, or 2;
m is 0 to 350;
n is 1 to 75;
v is 1 to 100; and
w is 1 to 4;
provided that at least one of $R^4$ and $R^5$ is H and provided that $R^1$, $R^2$, $R^3$, T, L, J and G do not contain a basic group; and
wherein the pka value of the acidic substituent F on the monomer from which [C] is derived is less than 5.5.

In Formula (1), [A] is derived from any olefinically unsaturated polymerisable monomer which does not contain an ionisable or ionised functional group. [B] provides the pendant polyether functionality of the acidic co-polymer and [C] provides the acidic functionality either in free acid or salt form.

The acidic co-polymer of Formula (1) comprises a backbone with both pendant polyalkylene oxide and acidic functionalities wherein the pka value of the acidic substituent F on the monomer from which [C] is derived is less than 5.5.

The pK$_a$ value for the acidic substituent F in [C] is a measure of the acid strength of F where K$_a$ is defined as:

$$K_a = keq\ [H_2O] = \frac{[FH]}{[F^-][H_3O^+]}$$

wherein pK$_a$=−log K$_a$, and Keq is the equilibrium constant.

The acidic co-polymers of the present invention commonly comprise [B] in the range of from 20 to 95 weight %, more preferably from 30 to 80 weight % and most preferably from 40 to 70 weight % and [A] in the range of from 0 to 45 weight %.

[C] is preferably present in the range of from 1 to 80 weight %, more preferably from 1 to 60 weight % and most preferably from 5 to 50 weight %.

Preferably the molar ratios of [A] to [B] to [C], (m:n:v) respectively, are chosen such that the cloud point of the acidic co-polymer is greater than 0° C. more preferably greater than 15° C. and most preferably greater than 25° C.

The cloud point value is related to the solubility of the polymer in water and refers to the boundary at which liquid-liquid phase separation takes place in a mixture of two or more components indicated by a cloudiness of the solution due to the formation of aggregates that scatter light. The temperature at which a 1% by weight solution of a polymer in distilled water becomes cloudy is the cloud point temperature.

Preferably the acidic co-polymers of the present invention comprise from 40 to 90% by weight polyethylene oxide introduced by [B], more preferably from 50 to 80% by weight polyethylene oxide introduced by [B]. The exact level of polyethylene oxide required to achieve a cloud point in the preferred range depends on a number of factors. These include:

(i) The level and hydrophobicity of [A] in the acidic co-polymer.
(ii) The level, degree of neutralisation and hydrophobicity of acidic component [C] in the co-polymer.
(iii) The composition of [B] as defined by R$^2$, R$^3$ and X and the value of p in Formula (11).
(iv) Whether the acidic groups in the polymer are neutralised or not.
(v) The presence of organics or electrolytes in solution.

It is preferred that the anti-microbial agent/acidic co-polymer compositions of the present invention form a clear solution. That is, that the cloud point of the acidic co-polymers in the presence of an anti-microbial agent for example poly (hexamethylene biguanide) (PHMB), is preferably above 15° C. and more preferably above 25° C.

Whilst the value of q is preferably 15 to 1000, q is most preferably 20 to 400.

Whilst R$^1$, R$^2$ and R$^3$ are each independently H, optionally substituted C$_{1-20}$-alkyl or C$_{3-20}$-cycloalkyl, it is preferred that R$^1$, R$^2$ and R$^3$ are each H, unsubstituted, C$_{1-10}$-alkyl or C$_{3-8}$-cycloalkyl. Most preferably R$^1$ is H or CH$_3$, R$^2$ is H or CH$_3$, and R$^3$ is H or unsubstituted C$_{1-6}$-alkyl, especially H or CH$_3$.

R$^4$ and R$^5$ in repeating monomer units of X, maybe the same or different, and are each independently H or C$_{1-4}$-alkyl so long as at least one of R$^4$ and R$^5$ is H. Preferably one of R$^4$ and R$^5$ is H and the other is —CH$_3$ or —C$_2$H$_5$ with the result that X comprises oxyethylene units or a mixture of oxyethylene, oxypropylene and, or oxybutylene units. Most preferably R$^4$ and R$^5$ are both H, with the result that X comprises oxyethylene units.

The value of p in Formula (10) is preferably 3 to 50, most preferably 3 to 40 and most especially 3 to 25.

T is an optionally substituted substituent examples of which include CN, OH, F, Cl, Br, —OR$^6$, —C(O)R$^6$, —OC (O)R$^6$, —C(O)OR$^6$, —C(O)NR$^7$R$^8$ and aryl optionally substituted by —OC(O)R$^6$, F, Cl, Br, C$_{1-6}$-alkyl, —CH$_2$Cl or —C(O)OR$^6$.

R$^6$ is C$_{1-10}$-alkyl more preferably C$_{1-8}$-alkyl for example methyl, ethyl, propyl, butyl, isopropyl, isobutyl or tert-butyl optionally substituted by a ketone, ether, epoxide, silane or ketoester group.

R$^7$ and R$^8$ are each independently H, C$_{1-8}$-alkyl or C$_{3-8}$-cycloalkyl optionally substituted by —OH, ketone or alkyl ether groups, most preferably R$^7$ and R$^8$ are H, —CH$_3$ or C$_2$H$_5$.

Preferably T is of the formula C(O)OR$^6$, —C(O)NR$^7$R$^8$ or —OC(O)R$^6$ and most preferably T is C(O)OR$^6$, wherein R$^6$, R$^7$ and R$^8$ are as previously described.

Each L is an optionally substituted linking group which joins X to the hydrocarbyl polymer backbone of [B]. L can be a variety of linking groups and may be the same or different, examples of L preferably comprise one or more carbon and/or hetero atoms, for example nitrogen or oxygen. Examples of preferred linking groups represented by L include:

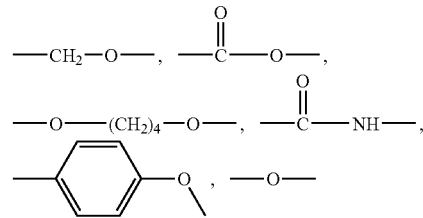

wherein the right hand side of the linking group is attached to X and the left hand side of the linking group is attached to the hydrocarbyl backbone.

It is particularly preferred that each L is of formula:

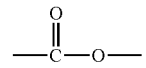

J is an optionally substituted hydrocarbyl group and may be the same or different. Examples of J include (shown with reference to [G]):

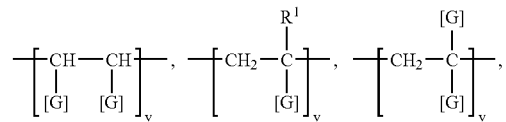

It is particularly preferred that J is of Formula:

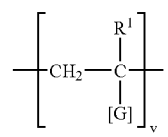

wherein R$^1$, v and G are as previously described.

F in Formula (12) is an acidic substituent. Each F is joined either directly to the hydrocarbyl group J or is linked to J by one or more linking groups G. When w is 2 to 4 in Formula (12), F may be joined directly to J in which case b (representing the proportion of G) is zero. Alternatively, F may be joined to the same or different carbon atoms of J by G. G may be the same or different in the repeat units of [C]. When G is present, it is preferably selected from linking groups which directly bond to J or by linking groups with one or more groups of atoms each group of which provides a chain of one or more atoms for linking [F] with [J] with the proviso that only one F can be directly linked to a single carbon atom in [J].

In cases where G represents one or more groups of atoms, G provides a linking chain of atoms. The chain will normally comprise one or more carbon atoms (for example in the form of an alkyl and/or aryl group), which may be optionally substituted by hetero atoms such as —N, —O, —S or P, most preferably N or O.

Examples of G linking groups (shown with reference to [F]) include:

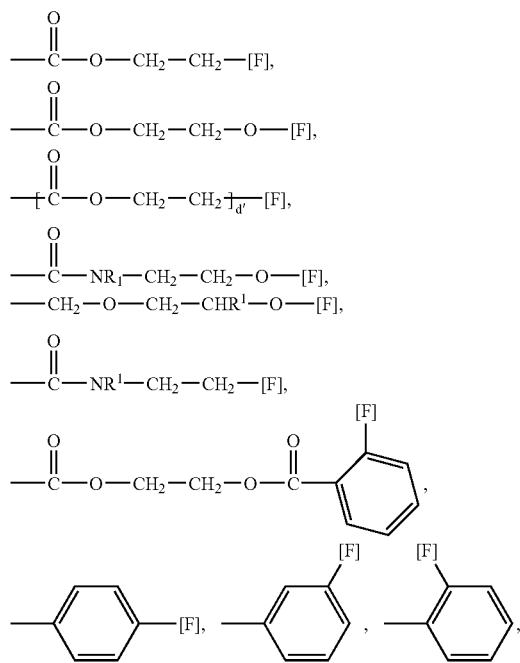

wherein d' is 2 or more, preferably 2, 3, 4 and 5 and F is the acidic substituent.

It is preferred that F is linked directly to J or that F is linked to J by one of the following preferred linking groups represented by G:

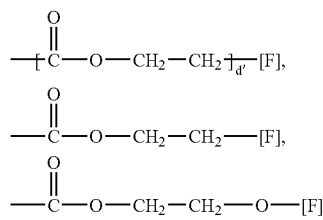

wherein d' and F are as previously described.

It is most especially preferred that F is linked directly to hydrocarbyl chain J in [C].

Examples of the acidic group F in Formula (12) include carboxylic acid, sulphonic acid, phosphonic acid and phosphoric acid. It is preferred that F comprises a carboxylic acid.

The values of m, n and v represent the molar composition of repeat units [A], [B] and [C] respectively in the polymer of Formula [1]. The value of m for [A] is preferably from 0 to 350, more preferably from 0 to 100 and most preferably from 0 to 50. The value of n for [B] is preferably from 1 to 75, more preferably from 1 to 40 and most preferably from 1 to 10. The value of v for [C] is preferably from 1 to 100, more preferably from 1 to 50 and most preferably from 1 to 40.

In accordance with the present invention it is a requirement that $R^1$, $R^2$, $R^3$, T, L, J, X and G do not contain a basic group. That is, for example, a primary, secondary or tertiary amine or salts or quaternised salts thereof, or any group that could be protonated by the acidic component F in [C]. Furthermore, it is a requirement of the present invention that the pka value of the acidic substituent [F] on the monomer from which [C] is derived is less than 5.5.

Examples of olefinically unsaturated monomers which may be used for [A] in Formula (1) include but are not limited to styrene, α-methyl styrene, acrylonitrile, methacrylonitrile, vinyl halides such as vinyl chloride, vinyl esters such as vinyl acetate, vinyl propionate, vinyl laurate, and vinyl esters of versatic acid such as VeoVa™ 9 and VeoVa™ 10 (available from Resolution Performance Products), vinyl ethers of heterocyclic vinyl compounds and in particular, esters of acrylic acid and methacrylic acid. Olefinically unsaturated monomers with additional functionality for subsequent crosslinking and/or adhesion promotion for use in the present invention may also be used. Examples of such monomers include diacetone acrylamide, acetoacetoxy ethyl methacrylate, glycidyl methacrylate, 2-hydroxy ethyl (meth)acrylate, 4-hydroxy butyl (meth)acrylate, 3-hydroxy propyl (meth)acrylate and hydroxy stearyl (meth)acrylate.

Examples of olefinically unsaturated monomers which may be used for [B] in Formula (1) include but are not limited to vinyl polyethers of ethylene or propylene oxide, for example hydroxypolyethoxy (5) polypropoxy (5) monoallyl ether (BX-AA-E5P5 available from Bimax), methoxypolyethyleneglycol 350 methacrylate (available under the trade name from Laporte), methoxypolyethyleneglycol 550 methacrylate (available under the trade names Bisomer MPEG 350MA and Bisomer MPEG 550MA from Laporte), methoxypolyethyleneglycol 350 acrylate, polyethyleneglycol (6) methacrylate PEM6 and polyethyleneglycol (6) acrylate PEA6.

Examples of olefinically unsaturated monomers which may be used for [C] in Formula (1) include but are not limited to acrylic acid, methacrylic acid, itaconic acid, maleic acid, fumaric acid, β-carboxy ethyl acrylate, sodium 1-allyloxy-2-hydroxy propane sulphonate. Sulphonic, phosphonic or phosphoric acid-bearing monomers may also be used, for example styrene ρ-sulphonic acid (or the corresponding styrene ρ-sulphonyl chloride). An acid bearing monomer from which [C] is derived may be polymerised as the free acid or as a salt, for example, the ammonium or alkali metal salts of ethylmethacrylate-2-sulphonic acid (available from Laporte as Bisomer SEM), 2-acrylamido-2-methylpropane sulphonic acid.

Preferred acidic co-polymers for use in the present invention are based on acrylic co-polymers, that is polymers based on acrylic or methacrylic acid and esters thereof.

Preferably [A], [B] and [C] in Formula (1) have the Formulae (13), (14) and (15) respectively, wherein:
[A] is of Formula (13),

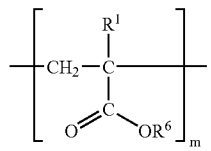

Formula (13)

[B] is of Formula (14), and

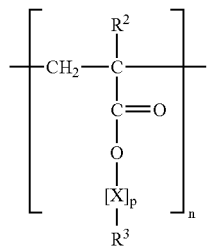

Formula (14)

[C] is of Formula (15),

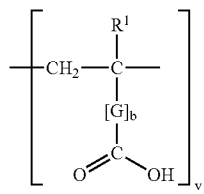

Formula (15)

wherein:
$R^6$ is $C_{1-10}$-alkyl more preferably $C_{2-4}$-alkyl optionally substituted by a ketone, ether, —OH, epoxide, silane or ketoester group; and
$R^1$, $R^2$, $R^3$, $R^6$, m, n, v, X, and p are as hereinbefore defined.

Preferred olefinically unsaturated monomers which may be used for [A] in Formula (13) are methyl acrylate, methyl methacrylate, ethyl acrylate, ethyl methacrylate, n-butyl acrylate, n-butyl methacrylate, isobutyl methacrylate, 2-ethylhexyl acrylate, 2-ethylhexyl methacrylate, isopropyl acrylate, isopropyl methacrylate, n-propyl acrylate, n-propyl methacrylate, t-butyl methacrylate, 2-ethylhexyl methacrylate, isobornyl methacrylate, cyclohexyl methacrylate and the corresponding acrylates. Methacrylates or acrylates having optional substitution on $R^6$ such as for example epoxide, alkyl ether, and aryl ether groups, hydroxyalkyl groups for example hydroxyethyl, hydroxy propyl or hydroxy butyl and modified analogues may also be employed as part of [A] of Formula (13). Ketofunctional monomers for example the acetoacetoxy esters of hydroxyalkyl acrylates and methacrylates for example acetoacetoxyethyl methacrylate as well as silane functional monomers for example 2-(trimethylsiloxy)ethyl methacrylate may also be used. The advantages of using a functionalised monomer is that it provides subsequent crosslinkability or adhesion promotion in the resulting polymer.

Examples of the preferred acrylic monomers which may be used for monomer [B] of Formula (14), include methoxypolyethyleneglycol 350 methacrylate, methoxypolyethyleneglycol 550 methacrylate (available from Laporte under the trade name Bisomer MPEG 350MA and Bisomer MPEG 550MA), methoxypolyethyleneglycol 350 acrylate, polyethyleneglycol (6) methacrylate PEM6 and polyethyleneglycol (6) acrylate PEA6.

Examples of preferred acrylic monomers which may be used for [C] of Formula (15) include methacrylic acid, acrylic acid and β-carboxy ethyl acrylate.

As illustrated in FIG. (1) the acidic co-polymers of the present invention comprise a vinyl backbone with pendant side-chains. Preferred acidic co-polymers of the present invention preferably comprise from 40% to 70% by weight of [B], from 5% to 50% of [C] and from 0 to 45% of [A].

The acidic co-polymers used in the present invention may be prepared by any co-polymerisation method known in the art. Preferably, the co-polymerisation reaction is carried out in water, an organic solvent or a mixture of water and organic solvent using a free radical initiator. Suitable free-radical-yielding initiators include inorganic peroxides for example potassium, sodium or ammonium persulphate, hydrogen peroxide, or percarbonates; organic peroxides, for example acyl peroxides including for example benzoyl peroxide, alkyl hydroperoxides such as t-butyl hydroperoxide and cumene hydroperoxide; dialkyl peroxides such as di-t-butyl peroxide; peroxy esters such as t-butyl perbenzoate and mixtures thereof may also be used. The peroxy compounds are in some cases advantageously used in combination with suitable reducing agents (redox systems) such as sodium or potassium pyrosulphite or bisulphite, and iso-ascorbic acid. Azo compounds such as azoisobutyronitrile or dimethyl 2.2'-azo bis-isobutylate may also be used. Metal compounds such as iron.ethylene diamine tetracetic acid (EDTA) may also be usefully employed as part of the redox initiator system. Other free radical initiators include cobalt chelate complexes and particularly Co(II) and Co(III) complexes of porphyrins, dioximes and benzildioxime diboron compounds. It is also possible to use an initiator system partitioning between the aqueous and organic phases, for example a combination of t-butyl hydroperoxide, iso-ascorbic acid and iron.ethylene diamine tetracetic acid. Preferred initiators comprise azo compounds such as azo-iso-butyronitrile or dimethyl 2,2'-azo bis-isobutylate and peroxides such as hydrogen peroxide or benzoyl peroxide. The amount of initiator or initiator system conventionally used is for example within the range of from 0.05 to 6 weight %, more preferably from 0.1 to 3% and most preferably from 0.5 to 2% by weight based on the total vinyl amount of monomers used.

The organic solvent is preferably a polar organic solvent and may be a ketone, alcohol or an ether. Examples of suitable polar solvents are methyl ethyl ketone, acetone, methyl isobutylketone, butyl acetate, ethoxyethylacetate, methanol, ethanol, n-propanol, iso-propanol, n-butanol, amyl alcohol, diethylglycol mono-n-butyl ether and butoxyethanol. Alternatively, the polar organic solvent may also be used with a non-polar organic liquid.

Suitable non-polar organic solvents include toluene-xylene mixtures and methylenechloride-dimethylformamide mixtures. Most preferably, the co-polymerisation reaction is carried out in aqueous alcoholic solvents for example, methanol, ethanol, n-propanol, iso-propanol, n-butanol, amyl alcohol, diethylglycol or butoxyethanol, most preferably aqueous ethanol mixtures.

When prepared by solution polymerisation the number average molecular weight (Mn) of the polymer is typically in the range 5,000 to 200,000, more preferably 10,000 to 100,000.

The acidic co-polymers can also be made by aqueous emulsion or suspension polymerisation (as described in *Principles of Polymerisation*, G Odian, Wiley, Interscience, 3$^{rd}$ edition, 1991), in which case the value of Mn may be higher and in the range 20,000 to 500,000.

According to the present invention a preferred anti-microbial agent for use in a composition with an acidic co-polymer of Formula (1) as hereinbefore described comprises an antibacterial agent, more preferably a linear polymeric biguanide which is a mixture of polymer chains in which the individual polymer chains, excluding the terminating groups are of Formula (6) or a salt thereof as hereinbefore described. A preferred linear polymeric biguanide for use in the present invention is poly(hexamethylenbiguanide)hydrochloride (PHMB) available from Avecia Limited under the trade name Vantocil™IB.

The amount of polymeric biguanide used in the composition of the present invention relative to the amount of acidic co-polymer is dependent upon the end use of the composition, the conditions under which it will be stored and the nature of the surface to which the composition is to be applied. The weight ratio of the linear polymeric biguanide to acidic co-polymer in the composition may vary over wide limits for example from 100:1 to 1:1000, more preferably from 20:1 to 1:500.

It is especially preferred that the ratio of linear polymeric biguanide group to acidic co-polymer in the antimicrobial composition is from 1:1 to 1:200.

The concentration of linear polymeric biguanide, for example poly(hexamethylene biguanide) (PHMB) used in the composition of the present invention is in the range of from 0.001 weight % to 25 weight %, preferably from 0.005 weight % to 10 weight %, and especially from 0.01% to 5 weight %. The pH of the composition is typically chosen so that it is most appropriate for a particular application and is preferably in the range of from pH 1 to 12 most preferably from pH 3 to 9.

The composition of the present invention may also contain other additives depending upon the particular use intended for the composition. Additional components optionally included in the composition may be for example additional polymeric materials, detergents, botanical extracts, perfumes, fragrances, thickeners, humectants, anti-corrosion agents, surfactants, colourants, chelating agents, buffers, acidity and alkalinity regulators, wetting agents, sequestering agents, hydrotropes, adjuvants, anti-soil agents and enzymes.

For ease of handling and dosing, it is generally convenient to combine the linear polymeric biguanide and acidic co-polymer into a formulation with a suitable carrier. The carrier may be a solid but is preferably a liquid and the formulation is preferably a solution, suspension or emulsion of the anti-microbial composition in the liquid.

Whilst water is the preferred carrier for the composition, it is possible that other solvents such as water miscible organic solvents may also be present in the composition. Examples of suitable water-miscible organic solvents include, glycols such as ethylene glycol, propylene glycol, dipropylene glycol methanol, ethanol, propan-1-ol, propan-2-ol, $C_{1-6}$-alkyl esters for example butylethyl acetate, pentyl acetate, N-methyl-2-pyrrolidone and lower $C_{1-4}$-alkyl carbitols such as methyl carbitol. Preferred water-miscible organic solvents are glycols with 2 to 6 carbon atoms, poly-alkylene glycols with 4 to 9 carbon atoms or mono $C_{1-4}$-alkyl ethers of glycols with 3 to 13 carbon atoms. The most preferred water-miscible organic solvents are propylene glycol, ethyl hexyl glycol, ethanol, butyl ethyl acetate or pentyl acetate.

Therefore according to a second aspect of the present invention there is provided a formulation comprising:
(i) a linear polymeric biguanide;
(ii) an acidic co-polymer; and
(iii) a carrier.

A preferred formulation of the final diluted application liquor according to a second aspect of the invention comprises from 0.01 to 5% by weight linear polymeric biguanide, more preferably from 0.1 to 1% by weight linear polymeric biguanide in the form of poly(hexamethylene biguanide)hydrochloride (PHMB). The amount of acidic co-polymer in the formulation is preferably from 0.01 to 50% by weight, especially from 0.1 to 25% by weight. The preferred carriers are water or water/alcohol mixtures. The pH of the formulation is typically chosen to be most appropriate for the application and is preferably in the range of from 1 to 12. Most preferably the pH of the formulation is in the range of from 3 to 9. An especially preferred formulation according to the second aspect of the present invention comprises a diluted application solution containing 0.5% by weight poly(hexamethylene biguanide)hydrochloride (PHMB) and from 2 to 15% by weight acidic co-polymer in the form of an aqueous solution.

The formulation may also contain other additives depending upon the particular use intended for the composition. Additional components optionally included in the formulation are for example those disclosed for use in compositions according to the first aspect of the invention.

During the course of the present studies it has surprisingly been found that when a composition comprising a linear polymeric biguanide and an acidic co-polymer is applied to a surface a sustained anti-microbial effect against a broad range of micro-organisms including gram positive bacteria, gram negative bacteria, pathogenic bacteria, yeasts, fungi and algae is achieved. Therefore, according to a further aspect of the present invention there is provided a method of treating a surface which comprises treating the surface with a composition or a formulation as hereinbefore described with reference to the first and second aspects of the present invention.

The preferred anti-microbial agent, poly(hexamethylene biguanide)hydrochloride, may be the only microbiologically active compound present in the composition or formulation. Alternatively, other microbiologically active compounds may also be present in combination with the polymeric biguanides. Examples of other microbiologically active compounds include for example: quaternary ammonium compounds for example, N,N-diethyl-N-dodecyl-N-benzylammonium chloride, N,N-dimethyl-N-octadecyl-N-(dimethyl benzyl)ammonium chloride, N,N-dimethyl-N,N-didecylammonium chloride, N,N-dimethyl-N,N-didodecylammonium chloride; N,N,N-trimethyl-N-tetradecylammonium chloride, N-benzyl-N,N-dimethyl-N—($C_{12}$-$C_{18}$ alkyl)ammonium chloride, N-(dichlorobenzyl)-N,—N-dimethyl-N-dodecylammonium chloride, N-hexadecylpyridinium chloride, N-hexadecyl pyridinium bromide, N-hexadecyl-N,N,N-trimethylammonium bromide, N-dodecyl pyridinium chloride, N-dodecylpyridinium bisulphate, N-benzyl-N-dodecyl-N,N-bis(beta-hydroxy-ethyl)ammonium chloride, N-dodecyl-N-benzyl-N,N-dimethylammonium chloride, N-benzyl-N,N-dimethyl-N—($C_{12}$-$C_{18}$ alkyl) ammonium chloride, N-dodecyl-N,N-dimethyl-N-ethylammonium ethylsulphate, N-dodecyl-N,N-dimethyl-N-(1-naphthylmethyl)ammonium chloride, N-hexadecyl-N,N-dimethyl-N-benzylammonium chloride, N-dodecyl-N,N-dimethyl-N-benzylammonium chloride or 1-(3-chloroallyl)-3,5,7-triaza-1-azonia-adamantane chloride, cocoalkylbenzyl-dimethylammonium, tetradecylbenzyldimethyl ammonium chlorides, myristyltrimethyl ammonium or cetyltrimethylammonium bromides, monoquaternary heterocyclic amine salts such as laurylpyridinium, cetylpyridinium or ($C_{12}$-$C_{14}$)alkyl benzylimidasolium chlorides; urea derivatives for example, 1,3-bis(hydroxymethyl)-5,5-dimethylhydantoin, bis(hydroxymethyl)urea, 3-(3,4-dichlorophenyl)-1,1-dimethylurea (Diuron), 3-(4-isopropylphenyl)-1,1-dimethylurea, tetrakis(hydroxymethyl)-acetylenediurea, 1-(hydroxymethyl)-5,5-dimethylhydantoin or imidazolidinylurea; amino compounds for example, 1,3-bis(2-ethylhexyl)-5-methyl-5-aminohexahydro-pyrimidine, hexamethylenetetramine, 1,3-bis(4-aminophenoxy)propane, dodecylamine or 2-[(hydroxymethyl)-amino]ethanol; imidazole derivatives for example 1 [2-(2,4-dichloro-phenyl)-2-(2-propenyloxy)ethyl]-1H-imidazole or 2-(methoxycarbonyl-amino)-benzimidazole (Carbendazim); nitrile compounds for example, 2-bromo-2-bromomethyl-glutaronitrile, 2-chloro-2-chloro-methylglutaro-nitrile, 1,2-dibromo-2,4-dicyanobutane or 2,4,5,6-tetrachloro-1,3-benzenedicarbonitrile (Chlorothalonil); thiocyanate derivatives for example methylene(bis)thiocyanate or 2-(thiocyanomethylthio)-benzothiazole; tin compounds or complexes for example, tributyltinoxide chloride, naphthoate, benzoate or 2-hydroxybenzoate; isothiazolin-3-ones, for example 4,5-trimethylene-4-isothiazolin-3-one, 2-methyl-4,5-trimethylene-4-isothiazolin-3-one, 2-methyl-4-isothiazolin-3-one (MIT), 5-chloro-2-methyl-4-isothiazolin-3-one (CMIT), 2-octyl-isothiazolin-3-one (OIT) or 4,5-dichloro-2-octyl-4-isothiazolin-3-one (DCOIT); benzisothiazolin-3-one compounds for example 1,2-benzisothiazolin-3-one (BIT), 2-methylbenzisothiazolin-3-one, 2-n-butylbenzisothiazolin-3-one, N-ethyl, N-n-propyl, N-n-pentyl, N-cyclopropyl, N-isobutyl, N-n-hexyl, N-n-octyl, N-n-decyl and N-tert-butyl1,2-benzisothiazolinone; thiazole derivatives for example, 2-(thiocyano methylthio)-benzthiazole or mercaptobenzthiazole; nitro compounds for example, tris(hydroxymethyl)nitromethane, 5-bromo-5-nitro-1,3-dioxane or 2-bromo-2-nitropropane-1,3-diol (Bronopol); iodine compounds, for example tri-iodo allyl alcohol; aldehydes and aldehyde release agents, for example glutaraldehyde (pentanedial), formaldehyde or glyoxal; amides for example chloracetamide, N,N-bis(hydroxymethyl)chloracetamide, N-hydroxymethyl-chloracetamide or dithio-2,2-bis(benzmethylamide); guanidine derivatives for example 1,6-hexamethylene-bis[5-(4-chlorophenyl)biguanide], 1,6-hexamethylene-bis[5-(4-chlorophenyl)guanide], bis(guanidinooctyl)amine triacetate, 1,6-D-(4'-chlorophenyldiguanide)-hexan (Chlorhexidine), polyoxyalkylene-guanidin-hydrochloride, polyhexamethyleneguanidine hydrochloride (PHMG), poly-(2-(2-ethoxy) ethoxyethyl guanidium chloride (PEEG) or dodecyl guanidine hydrochloride; thiones for example 3,5-dimethyltetrahydro-1,3,5-2H-thiodiazine-2-thione; sulphamides, for example N-dimethyl-N'-phenyl-(fluorodichloromethylthio) sulphamide (Preventol A4); triazine derivatives for example hexahydrotriazine, 1,3,5-tri-(hydroxyethyl)-1,3,5-hexahydrotriazine, 6-chloro-2,4-diethyl-amino-s-triazine or 4-cyclopropylamino-2-methylthio-6-t-butylamino-s-triazine (Irgarol); oxazolidine and derivatives thereof for example bis-oxazolidine; furan and derivatives thereof for example 2,5-dihydro-2,5-dialkoxy-2,5-dialkylfuran; carboxylic acids and the salts and esters thereof for example sorbic acid and 4-hydroxybenzoic acid; phenol and derivatives thereof for example 5-chloro-2-(2,4-dichloro-phenoxy)phenol, thio-bis (4-chlorophenol), 2-phenylphenol, 2,4,5-trichloro-2'-hydroxy-diphenylether (Triclosan) and 4-chloro-3,5-dimethylphenol (PCMX); sulphone derivatives for example diiodomethyl-paratolylsulphone, 2,3,5,6-tetrachloro-4-(methylsulphonyl)pyridine or hexachlorodimethylsulphone; imides for example, N-(fluorodichloromethylthio)phthalimide (Preventol A3), N-(trichloromethylthio)phthalimide (Folpet) or N-(trichloromethyl)thio-4-cyclohexene-1,2-dicarboxyimide (Captan); thioamides the metal complexes and salts thereof for example dimethyldithiocarbamate, ethylenebis-dithiocarbamate, 2-mercapto-pyridine-N-oxide (especially the 2:1 zinc complex and the sodium salt); azole fungicides for example hexaconazole, tebuconazole, propiconazole, etaconazole or tetraconazole; strobilurins, for example methyl-(E)-2-[2-(6-(2-cyanophenoxy)pyrimidin-4-yloxy)phenyl]-3-methoxyacrylate (Azoxystrobin), methyl-(E)-methoxyimino[α-(o-tolyloxy)-o-tolyl]acetate, N-methyl-(E)-methoxyimino[2-(2,5-dimethylphenoxymethyl) phenyl]acetamide, N-methyl-(E)-2-methoxyimino-2-(2-phenoxyphenyl)acetamide (Metominostrobin) or Trifloxystrobin; amides for example dithio-2,2'-bis(benzmethylamide) (Densil P) or 3,4,4'-Trichlorocarbanilide (Triclocarban); carbamates for example 3-lodopropargyl-N-butylcarbamate (IPBC), 3-lododpropargyl-N-phenylcarbamate (IPPC) or Bis-(diemthylthiocarbamoyl)-disulphide (Thiram); pyridine derivatives for example sodium or zinc salt of 2-mercaptopyridine-N-oxide (Sodium or Zinc pyrithione); compounds with activated halogen groups for example tetrachloroisophthalodintril (Chlorthalonil), 1,2-Dibromo-2,4-dicyanobutane (Tektamer 38); orgaonometallic compounds for example 10,10'-Oxybisphenoxyarsine (OBPA).

The amount of additional anti-microbial compound(s) in the composition will depend upon the nature of the additional anti-microbial compound and the surface to be protected against microbial degradation.

It is further possible to use combinations of two or more acidic co-polymers of Formula (1) as previously described in combination with the anti-microbial agents as previously described for the compositions or formulations of the present invention for disinfecting surfaces found in for example household, industrial or institutional areas. The treatment can be applied to a wide variety of surfaces as exemplified as follows but not limited thereto. Surface applications include for example, walls, floors, work surfaces, equipment found in domestic, industrial, food processing, sanitary, health and medical environments, skin, synthetic and natural textiles and fibres, stainless steel, polymer and polymeric coatings such as vinyl, polyvinyl chloride, polypropylene and polyethylene, wood, glass, rubber, paint surfaces, stone, marble, grouts, packaging and films.

As hereinbefore described the anti-microbial compositions and formulations according to the first and second aspects of the invention significantly reduces the levels of micro-organisms on surfaces treated with the anti-microbial compositions, which activity is sustained over a period of time.

According to a fourth aspect of the present invention there is therefore provided the use of a composition according to the first aspect of the present invention or the use of a formulation according to a second aspect of the present invention for the treatment of surfaces.

It has also been found that the acidic co-polymers described above in relation to the present invention may also be used in combination with anti-fungal compounds. It has surprisingly been found that fungicidal compounds are also controllably released from the acidic co-polymers over time thereby providing sustained and effective anti-fungal control.

Fungicides

A wide variety of fungicides can be used in combination with the acidic co-polymers described above. Examples of such fungicides include but are not limited to: methoxyacrylates, for example, methyl (E)-2-2-6-(2-cyanophenoxy)pyrimidin-4-yloxyphenyl-3-methoxyacrylate; carboxamides and acetamides for example, 5,6-dihydro-2-methyl-N-phenyl-1,4-oxathiin-3-carboxamide and 2-cyano-N-[(ethylamino)carbonyl]-2-(methoxyamino)acetamide; aldehydes, for example cinnamaldehyde and 3,5-dichloro-4-hydroxybenzaldehyde; pyrimidines, for example 4-cyclopropyl-6-methyl-N-phenyl-2-pyrimidinamine and 5-butyl-2-ethylamino-6-methylpyrimidin-4-ol; morpholines for example, (E,Z)4-[3-(4-chlorophenyl)-3-(3,4-dimethoxyphenyl)acryloyl]morpholine and $C_{11-14}$-alkyl-2,6-dimethylmorpholine-homologues such as (Tridemorph) and (±)-cis-4-[3-tert-butylphenyl)-2-methylpropyl]-2,6-dimethylmorpholine (Fenpropimorph); guanidines, for example 1-dodecylguanidine acetate; pyrroles, for example 4-(2,2-difluoro-1,3-bezodioxol-4-yl)-1Hpyrrole-3-carbonitrile; imidazoles and benzimidazoles, for example 1-[2-(2,4-dichlorophenyl)-2-(2-propenyloxy)ethyl]-1H-imidazole, 3-(3,5-dichlorophenyl)-N-(1-methylethyl)-2,4-dioxo-1-imidazolidinecarboxamide, Carbendazim (MBC), Benomyl, Fuberidazole, Thiabendazole, 1-(N-propyl-N-(2-(2,4,6-(trichlorophenoxy)-ethyl)-carbamoyl)-imidazole (prochloraz) and salts thereof; alanine derivatives for example, N-(2,6-dimethylphenyl)-N-(methoxyacetyl)-D-alaninemethyl ester and N-(2,6-dimethylphenyl)-N-(methoxyacetyl)-DL-alaninemethyl ester; triazoles for example, 1-[[2-(2,4-dichlorophenyl)-4-propyl-1,3-dioxolan-2-yl]methyl]-1H-1,2,4-triazole, H-1,2,4-triazole-1-ethanol-alpha-[2-(4-chlorophenyl)-ethyl]-alpha-(1,1-dimethylethyl), 1-[2-(2,4-dichlorophenyl)-1,3-dioxolan-2-yl-methyl]-1H-1,2,4-triazole [azaconazole], 1-(4-chlorophenoxy)-3,3-dimethyl-1-(1H-1,2,4-triazol-1-yl)-2-butanone (triadimefone), β-(4-chlorophenoxy)-α-(1,1-dimethyl-ethyl)-1H-1,2,4-triazole-1-ethanol (triadimenol), α-[2-(4-chlorophenyl)-ethyl]-α-(1,1-dimethylethyl)-1H-1,2,4-triazole-1-ethanol (tebuconazole), (RS)-2-(2,4-dichlorophenyl)-1-(1H-1,2,4-triazol-2-yl)-hexan-2-ol (hexaconazole), 1-[[2-(2,4-dichlorophenyl)-4-n-propyl-1,3-dioxolan-2-yl]-methyl]-1-H-1,2,4-triazole (propiconazole). Triazole fungicides can be present not only in the form of free bases but also in the form of their metal salt complexes or as acid addition salts, for example salts of metals of main groups II to IV and sub-groups I and II and IV to VII of the periodic table of elements, examples of which may include copper, zinc, manganese, magnesium, tin, iron, calcium, aluminium, lead, chromium, cobalt and nickel. Possible anions of the salts are those which are preferably derived from the following acids: hydrohalic acids, for example, hydrochloric acid, hydrobromic acid, phosphoric acid, nitric acid and sulphuric acid. In cases where the compound has an asymmetric carbon atom, isomers and isomer mixtures are also possible. Further examples of fungicides include: oxazolidines for example, 3-(3,5-dichlorophenyl)-5-methyl-5-vinyl-1,3-oxazolidine-2,4-dione; p-hydroxybenzoates for example, benzoic acid, paramethylbenzoic acid, salicylic acid, dehydroacetic acid and salts thereof; isothiazolinones, for example 2-methylisothiazolin-3-one, 5-chloro-2-methylisothiazolin-3-one, 4,5-dichloro-N-octyl-isothiazolin-3-one, 2-n-octyl-4-isothiazolin-3-one, cyclopentenisothiazolinones; benzisothiazolin-3-one compounds for example 2-methylbenzisothiazolin-3-one, 2-n-butylbenzisothiazolin-3-one N-ethyl, N-n-propyl, N-n-pentyl, N-n-hexyl, N-cyclopropyl, and N-isobutylbenzisothiazolin-3-one; quaternary ammonium compounds for example, cocoalkylbenzyl-dimethylammonium, tetradecylbenzyldimethylammonium chlorides, myristyltrimethyl ammonium, cetyltrimethylammonium bromides, monoquaternary heterocyclic amine salts, laurylpyridinium, cetylpyridinium or ($C_{12}$-$C_{14}$)alkyl benzylimidasolium chlorides, benzyldimethyltetradecylammoniumchloride, benzyl-dimethyl-dodecylammoniumchloride, didecyl-dimethyl-ammoniumchloride, alkyl ammonium halides, for example lauryl trimethyl ammonium chloride and dilauryl dimethyl ammonium chloride, alkyl aryl ammonium halides such as octadecyl dimethyl benzyl ammonium bromide, ethyl dimethyl stearyl ammonium chloride, trimethyl stearyl ammonium chloride, trimethyl cetyl ammonium chloride, dimethyl ethyl lauryl ammonium chloride, dimethyl propyl myristyl ammonium chloride, dinonyl dimethyl ammonium chloride, didecyl dimethyl ammonium chloride, diundecyl dimethyl ammonium chloride, didecyl dimethyl ammonium chloride, dinonyly ethyl ammonium chloride, dimethyl ethyl benzyl ammonium chloride, 3-(trimethyxyosilyl)propyldidecylmethyl ammonium chloride, 3-(trimethyoxysilyl)propyloctadecycdimethyl ammonium chloride, dimethyl dioctyl ammonium chloride, didecyl dimethyl ammonium chloride, didodecyl dimethyl ammonium chloride, dimethyl ditetradecyl ammonium chloride, dihexadecyl dimethyl ammonium chloride, dimethyl dioctadecyl ammonium chloride, decyl dimethyl octyl ammonium chloride, dimethyl dodecyloctyl ammonium chloride, benzyl decyl dimethyl ammonium chloride, benzyl dimethyl dodecyl ammonium chloride, benzyl dimethyl tetradecyl ammonium chloride, decyl dimethyl(ethyl benzyl)ammonium chloride, decyl dimethyl (dimethyl benzyl)-ammonium chloride, (chlorobenzyl)-decyl dimethyl ammonium chloride, decyl-(decyl-(dichlorobenzyl)-dimethyl ammonium chloride, benzyl didecyl methyl ammonium chloride, benzyl didocyl methyl ammonium chloride, benzyl ditetradecyl methyl ammonium chloride, and benzyl dodecyl ethyl ammonium chloride; iodopropargyl derivatives for example, 3-iodo-2-propynyl-N-n-butylcarbamate (IPBC), propyl 3-(dimethylamino)propylcarbamate-hydrochlorides, 3-iodo-2-propynyl-N-n-propyl carbamate, 3-iodo-2-propynyl-N-n-hexyl carbamate, 3-iodo-2-propynyl-N-cyclohexylcarbamate, 3-iodo-2-propynyl-N-phenyl carbamate and thiocarbamates for example S-ethyl cyclohexyl(ethyl)thiocarbamate; sulphenamides for example, Dichlofluanid (Euparen), Tolylfluarid (Methyleuparen), Folpet, Fluorfolpet, tetramethyidiuramdisulfides (TMTD) and 2-methylbenzamide-1,1'disulphide (available as Densil™P from Avecia Ltd); thiocyanates for example, thiocyanatomethylthiobenzothiazole (TCMTB) and methylenbisthiocyanate (MBT); phenols for example, o-phenylphenol, tribromphenol, tetrachlorphenol, pentachlorphenol, 2-phenoxyethnaol 3-methyl-4-chlorphenol, dichlorophen and chlorphen; iododeriatives for example, diiodmethyl-p-arylsulfone and diiodmethyl-p-tolylsulfone; bromoderivatives for example, 2-bromo-2-nitro-1,3-propanediol(Bronopol) and 1,2-dibromo-2,4-dicyanobutane (Tektamer™38); pyridines for example, 1-hydroxy-2-pyridinthione or pyridine-2-thiol-1-oxide (sodium, iron, manganese or zinc salts commercially available under the trademark Sodium Omadine from Arch Chemicals), tetrachlor-4-methylsulphonylpyridine, 2,3,5,6 tetrachloro-4(methyl sulphonyl)pyridine (available from Avecia Limited as Densil™ S); metallic soaps for example, tin, copper, zinc-naphthenate, octoate, 2-ethylhexanoate, oleate, -phosphate, benzoate, or oxides for example TBTO, $Cu_2O$, CuO and ZnO; organic tin-derivatives, for example tributyltin naphthenate or tributyl tinoxide; dialkyldithiocarbamates for example sodium and zinc salts of dialkyldithiocarbamates; nitriles for example 2,4,5,6-tetrachlorisophthalonitrile (Chlorthalonil); benzthiazoles, for example 2-mercaptobenzothiazoles; Dazomet; chinolines for example 8-hydroxyquinoline; Tris-N-(cyclohexyldiazeniumdioxy)-aluminum, N-(cyclohexyldiazeniumdioxy)-tributyl tin or potassium salts and Bis-(N-cyclohexyl)diazinium (-dioxy-copper or aluminum); alkyl esters of parahydroxybenzoic acid particularly the methyl, ethyl, propyl and; 2,4,4'-trichloro-2-hydroxydiphenyl ether (available under the trade name Triclosan) or 4,4'-trichloro-2-hydroxydiphenyl ether available under the tradename Diclosan); formaldehyde release compounds for example hydantoins, N,N"-methylene bis[N'-(hydroxymethyl)-2,5-dioxo-4-imidazolidinyl]urea, Quaternium-15 and 1,3-dimethylol-5,5-dimethylhydantoin (DMDMH), N-(hydroxymethyl)-N-(1,3-dihydroxymethyl-2,5-dioxo-4-imidazolidinyl)-N'-(hydroxymethyl); urea and the cis isomer of 1-(3-chloroallyl)-3,5,7-triaza-1-azoniaadamantane chloride; benzylalcoholmono(poly)hemiformal, oxazolidine, hexahydro-s-triazine and N-methylolchloracetamid; cyclic thiohydroxamic acid compounds for example imidazolidine-2-thione, pyrrolinethione, pyrrolidinethione, isoindolinethione, 3-hydroxy-4-methylthiazol-2(3H)-thione, 3-hydroxy-4-phenylthiazol-2(3H)-thione, 3-hydroxy-4,5,6,7-tetrahydrobenzothiazol-2(3H)-thione, 5,5-dimethyl-1-hydroxy-4-imino-3-phenylimidazolidine-2-thione, 1-hydroxy-4-imino-3-phenyl-2-thiono-1,3-diazaspiro[4,5]-decane, 1-hydroxy-5-methyl-4-phenylimidazoline-2-thione, 4,5-dimethyl-3-hydroxythiazol-2(3H)-thione, 4-ethyl-3-hydroxy-5-methylthiazol-2(3H)-thione, 4-(4-chlorophenyl)-3-hydroxythiazol-2(3H)-thione, 3-hydroxy-5-methyl-4-phenylthiazol-2(3H)-thione, 1-hydroxypyrrolidin-2-thione, 5,5-dimethyl-1-hydroxypyrrolidin-2-thione and 2-hydroxy-2,3-dihyro-1H-isoindol-1-thione.

Preferred antifungal compounds include quaternary ammonium compounds, isothiazolione and benzisothiazolinone compounds, carbamates and pyridine compounds.

Therefore, according to an a fifth aspect of the present invention there is provided a composition comprising:
(i) a fungicide; and
(ii) an acidic co-polymer of Formula (1)

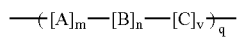

Formula (1)

wherein:
[A] is of Formula (9),

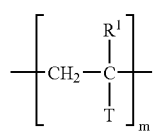

Formula (9)

[B] is of Formula (10),

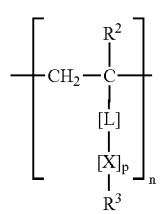

Formula (10)

and [C] is of Formula (12),

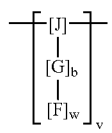

Formula (12)

wherein:
X is of Formula (11),

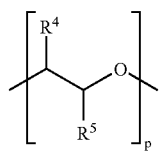

Formula (11)

wherein [A], [B] and [C] may occur in any order;
T is an optionally substituted substituent;
L and G each independently is an optionally substituted linking group;
$R^1$, $R^2$ and $R^3$ are each independently H, optionally substituted $C_{1-20}$-alkyl or optionally substituted $C_{3-20}$-cycloalkyl;
$R^4$ and $R^5$ are each independently H or $C_{1-4}$-alkyl;
q is 15 to 1000;
p is 3 to 50;
J is an optionally substituted hydrocarbyl, group;
F is an acidic substituent;
b is 0, 1, or 2;
m is 0 to 350;
n is 1 to 75;
v is 1 to 100; and
w is 1 to 4;
provided that at least one of $R^4$ and $R^5$ is H and provided that $R^1$, $R^2$, $R^3$, T, L, J and G do not contain a basic group; and
wherein the pka value of the acidic substituent F on the monomer from which [C] is derived is less than 5.5.

In the fifth aspect of the present invention preferences for [A], [B], [C], m, n, v, q, T, L, X, J, G, F, $R^1$, $R^2$, $R^3$, $R^4$, $R^5$, p, b and w are as hereinbefore defined with reference to the first aspect of the present invention.

The invention is further illustrated by the following examples in which all parts are by weight unless otherwise stated.

EXPERIMENTAL DETAILS

Preparation of Acidic Co-Polymers.
Preparation of Polymer Example 7 (Table 1).
A clean dry one liter glass reactor was fitted with an overhead stirrer, nitrogen bleed, thermocouple and condenser. Initiator solution (1) was prepared by dissolving dimethyl 2,2'azobis isobutyrate (2.3 g) (0.01 moles) in solvent (92.7 g of a 50/50 mixture of ethanol/distilled water). A monomer solution (2) containing solvent (251.2 g of a 50/50 mixture of ethanol/distilled water), methacrylic acid (68.8 g, 0.8 moles) and methoxy (polyethylene glycol 550) mono methacrylate (127 g, 0.2 moles) was also prepared. Into the reactor was added solvent (360 g of a 50/50 mixture of ethanol/distilled water) followed by monomer solution (2) (447 g). The monomer solution (2) was washed into the reactor with additional solvent (100 g of a 50/50 mixture of ethanol/distilled water).

The reactor was heated to 75° C. using a Haake circulating water bath and was stirred at 180 rpm under a nitrogen blanket. At time zero initiator solution (1) (23.7 g) was added to the reactor followed 30 minutes later by more initiator solution (47.5 g). The solution was left for 3 hours 30 minutes before increasing the reactor temperature to 80° C. On reaching the required temperature additional initiator solution (1) (11.9 g) was added to the reactor which was then stirred for a further two hours after which time the final aliquot of initiator solution (1) (11.9 g) was added. After two hours the resultant co-polymer solution was cooled and removed from the reactor.

The total time of polymerisation was eight hours. The final solution was water white and free of particulate matter. The co-polymer was formed in greater than 99% yield as determined by weight difference following exhaustive evaporation from a sample of the co-polymer solution.

The molecular weight of the co-polymer was determined using gel permeation chromatography (GPC) with polyethylene oxide as molecular weight standards. NMR Analysis was used to confirm the ratio of the repeat monomer units [A], [B] and [C] and Dynamic Mechanical Thermal Analysis (DMTA) was used to determine the Tg of the co-polymer. Polymers 1 to 14 in Table 1, containing different monomers [A], [B] and [C] in various molar ratios, were prepared according to the same procedure as outlined above.

TABLE 1

Composition of Acidic Co-polymers.

| Poly-mer | Monomers [A] | [B] | [C] | Length of PEG/PPG Units[1] | Molar Ratio of Repeat Units [A]:[B]:[C] | | |
|---|---|---|---|---|---|---|---|
| 1 | | PEG350MA | MAA | 8 | | 1 | 2 |
| 2 | | PEG350MA | MAA | 8 | | 1 | 3 |
| 3 | | PEG350MA | MAA | 8 | | 1 | 4 |
| 4 | | PEG350MA | MAA | 8 | | 1 | 5 |
| 5 | | PEG350MA | MAA | 8 | | 1 | 6 |
| 6 | | PEG550MA | MAA | 12 | | 1 | 3 |
| 7 | | PEG550MA | MAA | 12 | | 1 | 4 |
| 8 | | PEG1000MA | MAA | 23 | | 1 | 4 |
| 9 | | PEG1000MA | MAA | 23 | | 1 | 6 |
| 10 | | PEG1000MA | MAA | 23 | | 1 | 10 |
| 11 | BMA | PEG550MA | MAA | 12 | 1 | 2 | 6 |
| 12 | MMA | PPG350MA | AMPS | 8 | 4 | 1 | 1 |
| 13 | | PPG550MA | VinylPO3H | 12 | | 1 | 4 |
| 14 | MMA | PPG5MA | MAA | 5 | 4 | 1 | 2 |

The value [1] corresponds to (p) in formulae (10) and (11)
MAA Methacrylic Acid
BMA Butyl methacrylate
AMPS 2-acrylimido methyl propane sulphonic acid VinylPO3H Vinyl phosphonic acidPPG5MA Methoxypolypropylene glycol monomethacrylate with 5 propylene glycol units
PEG350MA Methoxy polyethylene glycol monomethacrylate with 7 to 8 ethylene oxide units.
PEG550MA Methoxy polyethylene glycol monomethacrylate with 12 to 13 ethylene oxide units.
Determination of the Cloud Point of the Acidic Co-Polymers of Table 1 and Cloud Point Changes with Co-Polymer Composition.

The cloud points of co-polymers (1 to 14 from Table 1) were determined by making 1% by weight solutions of the polymers in distilled water. Each polymer solution was heated and stirred until it became cloudy. The stirred solution was then allowed to cool whilst the temperature was monitored. The temperature at which the solution became clear is the cloud point. The cloud point of Polymer 10 determined by this method was 33° C. (polyethylene oxide content 65% by weight).

Figure 1 shows how the cloud point varies as a function of the polyethylene oxide (PEO) content in polymers 3, 7 and 8. Figure 1 illustrates the polymer cloud point variation as a function of PEO content and PEO chain length (value p in Formulate (10) and (11)).

From Figure 1 it can be concluded that for the acidic co-polymers the cloud point increases as the polyethylene oxide content increases from 56 to 65 to 76% by weight for co-polymers 3, 7 and 8 respectively.

Preparation of Acid Co-Polymer/Anti-Microbial Agent Compositions

Compositions 1 to 20 (in Table 2) were prepared by mixing a 20% aqueous solution of poly (hexamethylene biguanide) hydrochloride (PHMB) (5 g) (available from Avecia Limited as Vantocil™IB) to each of the polymers 1 to 20 from Table 1 as 20% solutions (in water/ethanol 1/1) in varying quantities as set out in Table 2. The compositions were allowed to stand for 24 hours before being applied to substrates such as glass or ceramic tiles. All of the compositions were low viscosity colourless transparent solutions, free from sediment and with excellent storage stability. Storage stability was tested by storing the compositions for 2 months at 52° C. and was considered excellent if the viscosity of the composition remained unchanged and there was no formation of precipitate or gel particles.

Preparation of basic Copolymer compositions with various biocides looking at antifungal properties using polymer Example 2.

Compositions 21-28 were prepared by mixing with various biocides. To a sample of the polymer solution the biocide was added at concentrations ranging from 0.1%-0.5% wt/wt on total weight of the solution. The compositions were placed on a rotating mixer for 24 hours to form a homogenious composition and then applied to substrates such as glass or ceramic tile. The compositions were of low viscosity and free from sediment.

TABLE 2

| Composition Number | Acidic Co-polymer Number (Table 1) | Acidic Co-polymer (weight %) | Polymeric biguanide (PHMB)/other Biocide(weight %) |
|---|---|---|---|
| 1 | 1 | 95 | 5 |
| 2 | 2 | 95 | 5 |
| 3 | 3 | 95 | 5 |
| 4 | 4 | 95 | 5 |
| 5 | 5 | 95 | 5 |
| 6 | 6 | 95 | 5 |
| 7 | 7 | 37.5 | 62.5 |
| 8 | 7 | 52.4 | 47.6 |
| 9 | 7 | 68.7 | 31.3 |
| 10 | 7 | 73.7 | 26.3 |
| 11 | 7 | 78.7 | 21.3 |
| 12 | 7 | 83.3 | 16.7 |
| 13 | 7 | 84.9 | 15.1 |
| 14 | 7 | 95 | 5 |
| 15 | 8 | 95 | 5 |
| 16 | 9 | 95 | 5 |
| 17 | 10 | 95 | 5 |
| 18 | 12 | 90 | 10 |
| 19 | 13 | 90 | 10 |
| 20 | 14 | 90 | 10 |
| 21 | 2 | 99.9 | 0.1 of Biocide A |
| 22 | 2 | 99.8 | 0.2 of Biocide A |
| 23 | 2 | 99.8 | 0.2 of Biocide B |
| 24 | 2 | 99.5 | 0.5 of Biocide B |
| 25 | 2 | 99.9 | 0.1 of Biocide C |
| 26 | 2 | 99.8 | 0.2 of Biocide C |

TABLE 2-continued

| Composition Number | Acidic Co-polymer Number (Table 1) | Acidic Co-polymer (weight %) | Polymeric biguanide (PHMB)/other Biocide(weight %) |
|---|---|---|---|
| 27 | 2 | 99.9 | 0.1 of Biocide D |
| 28 | 2 | 99.8 | 0.2 of Biocide D |

Biocide A n-Butyl 1,2, benzisothiazolin
Biocide B Dodecylethyldimethylammonium bromide
Biocide C 3-iodopropargylbutyl carbamate
Biocide D 2-octylisothiazolin-3-one Measurement of the Release of Anti-Bacterial Agent (PHMB) from Films of Acidic Co-Polymer HMB/Compositions.
Calibration of Poly(hexamethylene)biguanide (PHMB) Concentration by UV Spectrometry Firstly the UV absorbance at 236 nm of a known concentration of poly(hexamethylene biguanide) (PHMB) dissolved in water was measured (Perkin Elmer Lambda 900 UV/Vis/NIR Spectrophotometer). In a similar manner the UV absorbance at 236 nm was measured for a series of samples prepared from known dilutions of the original PHMB aqueous solution. A calibration curve for PHMB concentration in aqueous solution was produced (Figure 2) by plotting UV absorbance at 236 nm against PHMB concentration.

Figure 2:
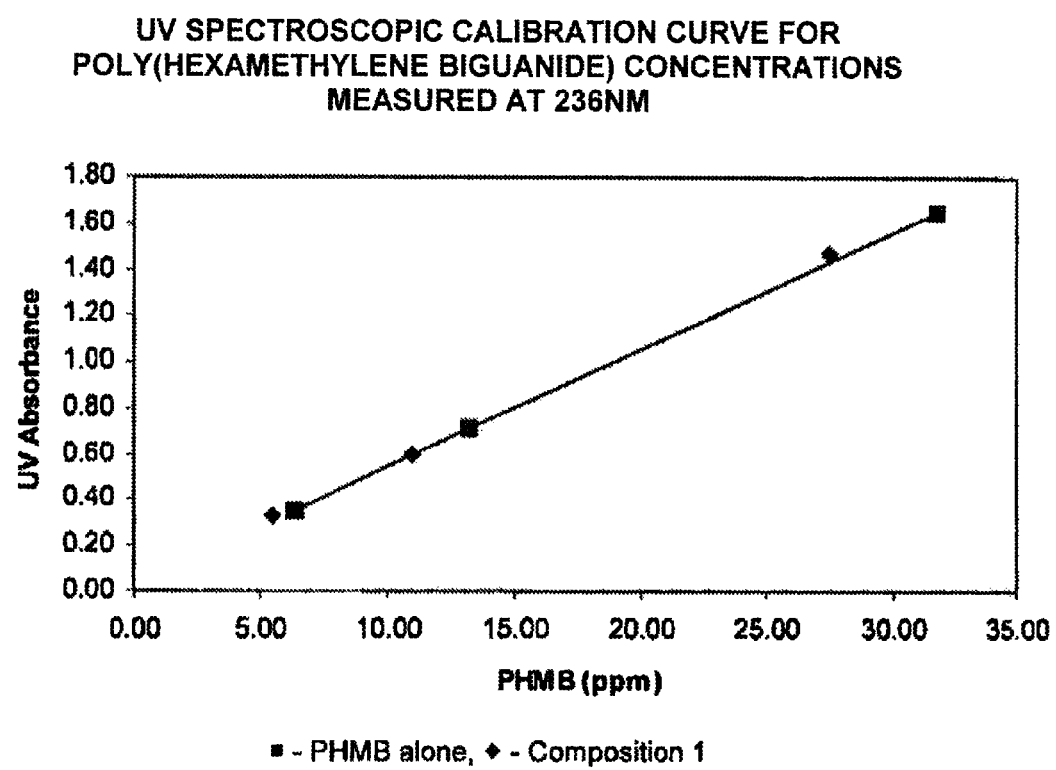
FIG. 2 illustrates the UV spectroscopic calibration curve for PHMB concentrations.

In addition a similar UV calibration curve (Figure 2) was produced for PHMB in the presence of acidic co-polymer composition 1, Figure 2 showed that the presence of acidic co-polymer did not significantly interfere with the determination of the PHMB concentration by this method.

General Method for the Measurement of the Rate of Poly (hexamethylene biguanide) (PHMB) Release from Films of Co-Polymer/PHMB Compositions 1 to 20 using UV Analysis.

Acidic co-polymer/PHMB Compositions 1 to 20 were separately applied to clean glass panels (150 mm×100 mm) and films of the composition were drawn down using a Sheen 250 µm draw down bar. The films were allowed to dry and the coating weight noted.

Each coated glass panel was immersed separately in distilled water (1 L) in a 2 L beaker and stirred at a constant speed using a magnetic stirrer.

Samples of water (approximately 5 cm$^3$) were taken from the beaker in duplicate at regular intervals over a one hour period.

The water samples were analysed using a UV spectrophotometer and the absorbance of each sample measured at a specific peak corresponding to the $\lambda$ max of poly(hexamethylene biguanide) (PHMB). The measured absorbance was directly related to the concentration of the PHMB in the beaker.

Using the methodology described above the following release profiles (Figures 3 and 4) were generated, Figure 3 illustrates the release of PHMB from coatings of PHMB/acidic co-polymer compositions 1 and 14. FIgure 4 illustrates the release of PHMB from coatings of PHMB/acidic co-polymer compositions 12 and 14 (Table 2) showing the effect of PHMB loading on the release rate of PHMB from the PHMB/co-polymer film.

Figure 3:
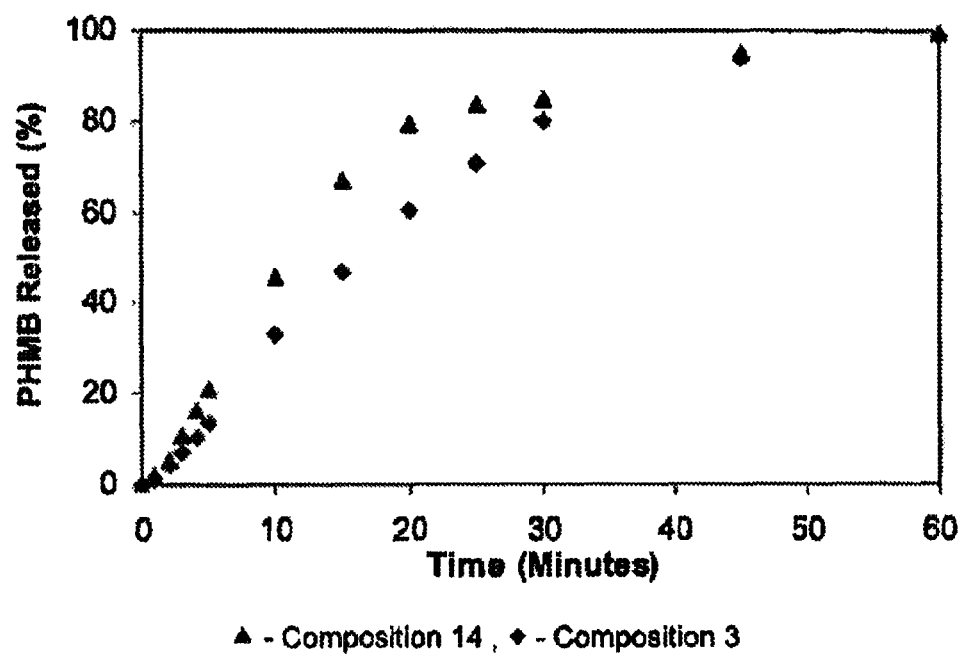
FIG. 3 illustrates the release of PHMB from coatings of PHMB/acidic co- polymer compositions.
Figure 4:
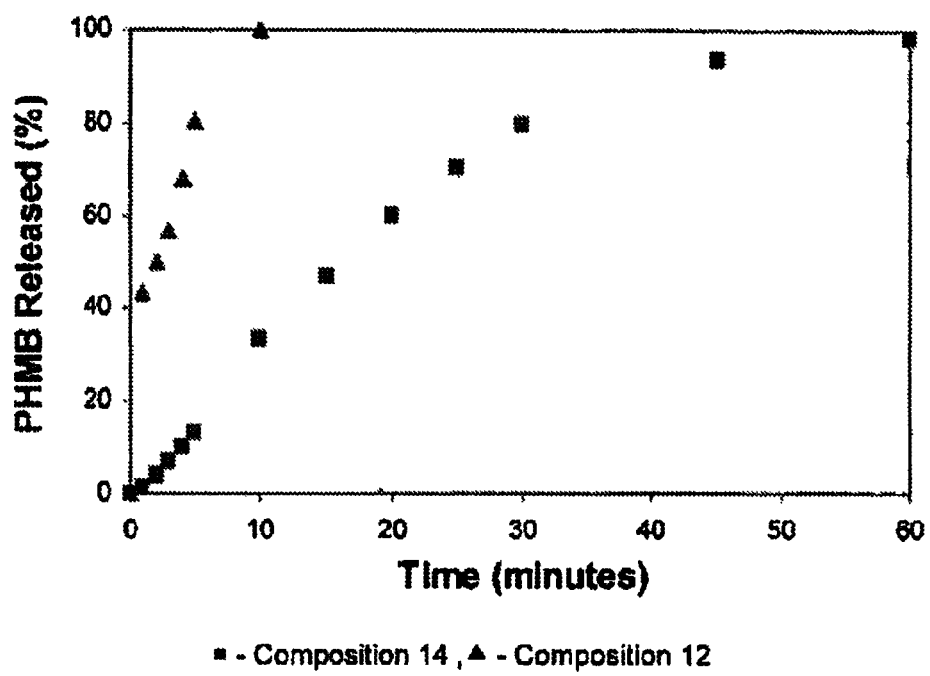
FIG. 4 illustrates the release of PHMB from coatings of PHMB/acidic co- polymer compositions showing the effect of PHMB loading on the release rate of PHMB from the PHMB/co-polymer film.

From Figure 3 the following can be concluded:
(i) Films of compositions 14 and 3 both demonstrate a controlled release of PHMB over a one hour period.
(ii) Films of compositions 14 and 3 release approximately 50% of the PHMB over a 15 minute period.
(iii) A film of composition 14 which contains the slightly more hydrophilic polymer 7 with a PEO content of 65% releases PHMB slightly faster than a film of composition 14 containing Polymer 3 with a PEO content of 56%.

From Figure 4 the following can be concluded:
(i) A film of composition 12 containing 16.7% by weight PHMB releases all its PHMB within 10 minutes whereas Composition 14 with just 5% by weight PHMB takes 60 minutes to fully release all PHMB.

Therefore, according to the present invention it was found that the rate of dissolution of PHMB from the acidic co-polymer/PHMB could be controlled according to the structure of the acidic co-polymer and the PHMB content. Moreover, the above illustrates that stable solutions in both water and water/ethanol mixtures can be prepared with acid bearing co-polymers and polymeric biguanides.

Calculation of Minimum Inhibitory Concentrations

The intrinsic antimicrobial activity of compositions of co-polymer example 7 from table 1 with various levels of PHMB were evaluated by measuring the Minimum Inhibitory Concentrations (MICs):
1. Bacteria (*Pseudomonas aeruginosa* ATCC 15442) were grown on nutrient agar for 16 to 24 hours at 37° C. (to give approximately 10$^9$ cells per ml).
2. A 0.1% (v/v) inoculum was used to seed fresh medium and 100 µl was then added to each well of a microtitre plate, except for the first well which contained 200 µl.
3. Using doubling dilutions, the concentration of the compounds under investigation were varied in each well along the ordinate axis.
4. The presence or absence of growth was determined by visual inspection after 24 hours incubation at 37° C.

The MIC is the lowest concentration of the sample required to inhibit bacterial growth.

TABLE 5

Intrinsic Activity of Acidic co-polymer, Example 7[1] with PHMB.

| Compositiuon Number | % by weight PHMB on acidic co-polymer | MIC versus *Pseudomonas aeruiginosa* (ppm PHMB.) |
|---|---|---|
| | 100 PHMB (Control) | 10 |
| 7 | 62.5 | 12 |
| 8 | 47.6 | 54 |
| 9 | 31.3 | 1200 |
| 10 | 26.3 | 1300 |
| 11 | 21.3 | 2100 |
| 13 | 15.1 | 1500 |

[1]for composition of Polymer example 7 see table 1.
Stable compositions could be prepared for all compositions used in the MIC's test protocol and as shown in the Table 5 an intrinsic activity could be achieved.

Sustained Bactericidal Activity of Acidic Co-polymers with PHMB
Experimental Determination of the Residual Bactericidal Activity of Acidic Co-Polymer/PHMB Formulations.

Acidic co-polymer/PHMB compositions were prepared as previously described (Table 2).

The residual antibacterial activity of the samples was determined by the following methodology:
1. All compositions were diluted to 0.5% active ingredient (PHMB). A 50 µl aliquot of each sample was placed in a ceramic tile well and allowed to dry for approximately 1 hour.
2. Bacteria (*Ps. aeruginosa* ATCC 15442) were grown in nutrient broth at 37° C. for 16-20 hours.
3. An inoculum of approximately 10$^8$ organisms per ml was prepared in physiological saline (0.85% NaCl).
4. A 150 µl aliquot of bacterial inoculum was pipetted into the ceramic tile well previously coated by the PHMB/polymer composition, and incubated at room temperature.

5. After 5 minutes contact time the inoculum was removed by pipette and the number of surviving, viable organisms enumerated (samples were serially diluted in CEN neutraliser by 10², a 1 ml aliquot was added to 9 ml of impedance broth and the RABIT™ was used to enumerate bacterial cells).
6. The PHMB/polymer coated ceramic wells were then washed up to five times with 5 ml aliquots of sterile distilled water.
7. Following each washing step, the samples were re-inoculated with a 150 µl aliquot of bacterial inoculum.
8. As above the inoculum was removed after 5 minutes and the number of viable organisms enumerated by the method described above.

The RABIT™ (Rapid Automated Bacterial Impedance Technique) measures the change in conductance of a bacterial suspension over time. Actively growing bacteria break down uncharged or weakly charged molecules in a defined media to give end products that are highly charged. The resultant increase in conductance can be directly related to bacterial concentration by the use of a calibration curve. (Further background relating to this known technique can be found in: Technical Reference Paper-RAB-03, Don Whitley Scientific, 14 Otley Road, Shipley, West Yorkshire, UK, BD17 7SE). Table 6 summarises the sustained bactericidal activity of the Acidic co-polymer/PHMB formulations obtained using the above technique.

TABLE 6

Sustained Bactericidal Activity of Anionic Co-polymers with PHMB.

| Composition Number | % PHMB by weight on anionic co-polymer | log reduction vs. Ps. aeruginosa @ 5 min | | |
|---|---|---|---|---|
| | | No washes | 1 wash | 2 washes |
| PHMB | 100 | 7.2 | 4.0 | 1.6 |
| 18 | 10 | 1.1 | 3.9 | 2.8 |
| 19 | 10 | 2.7 | 1.9 | 1.0 |
| 20 | 10 | 4.6 | 4.7 | 0.9 |

All composition gave stable formulations with the acidic copolymers.

Table 6 The composition 18 sustained its residual bactericidal effect compared with PHMB alone under the repeated washing regime used in the protocol.

Sustained Fungicidal Activity of Acidic co-polymers with Various Biocides

Experimental Determination of the Residual Fungicidal Activity of Acidic Co-Polymer/Biocide Formulations.

Acidic co-polymer/Biocide compositions were prepared as previously described (Table 2).

The residual antifungal activity of the compositions were determined by the following methodology:
1. Films of each composition were created on glass microscope slides using a '0' K-Bar and allowed to dry for no less than 24 hours.
2. Fungi (*Aspergillus niger* ATCC 16404) were grown on malt agar plates at 25° C. for approx. 7 days.
3. An inoculum of approximately 10⁷ spores per ml was prepared in physiological saline (0.85% NaCl).
4. A 150 µl aliquot of fungal inoculum was added to the surface of the compositions and incubated at room temperature for 24 hours.
5. The number of surviving, viable organisms were then enumerated (samples were washed into a neutralising medium, serially diluted in physiological saline and plated out onto malt agar).
6. Each composition was then washed ten times by spraying with sterile distilled water.
7. Each composition was then re-inoculated and after 24 hours the number of viable organisms enumerated by the method described above.

Table 7 summarises the sustained fungicidal activity of the Acidic co-polymer/Biocide formulations obtained using the above technique.

TABLE 7

Sustained Fungicidal Activity of Acidic Co-polymers (Example 2) with Various Biocides.

| Composition Number | Biocides | Weight Ratio (w/w) Biocide:polymer | log reduction vs. A. niger @ 24 hours | |
|---|---|---|---|---|
| | | | No washes | 10 washes |
| 22 | Biocide A | 499:1 | 0.4 | 0 |
| 24 | Biocide B | 199:1 | 3.4 | 3.4 |
| 26 | Biocide C | 499:1 | 3.4 | 0.2 |
| 28 | Biocide D | 499:1 | 3.4 | 0.5 |

It can be concluded that not only can stable formulations be prepared with the various biocides but that a sustained effect could be maintained using the spray washing protocol.

The results in Table 7 show that 1 formulation gave excellent sustained fungicidal activity.

While the invention has been described above with references to specific embodiments thereof, it is apparent that many change, modifications, and variations can be made without departing from the inventive concept herein. Accordingly, it is intended to embrace all such changes, modifications and variations that fall within the spirit and broad scope of the appended claims. All patent applications, patents and other publications cited herein are incorporated by reference in their entirety.

The invention claimed is:

1. A composition comprising:
   (i) an anti-microbial agent comprising a polymeric biguanide, alone or in combination with at least one other microbiologically active component selected from the group consisting of quaternary ammonium compounds, monoquaternary heterocyclic amine salts, urea derivatives, amino compounds, imidazole derivatives, nitrile compounds, tin compounds or complexes, isothiazolin-3-ones, thiazole derivatives, nitro compounds, iodine compounds, aldehyde release agents, thiones, triazine derivatives, oxazolidine and derivatives thereof, furan and derivatives thereof, carboxylic acids and the salts and esters thereof, phenol and derivatives thereof, sulphone derivatives, imides, thioamides, 2-mercapto-pyridine-N-oxide, azole fungicides, strobilurins, amides, carbamates, pyridine derivatives, compounds with active halogen groups, and organometallic compounds;
   wherein the polymeric biguanide is a linear polymeric biguanide comprising a mixture of polymer chains in which the individual polymer chains excluding the terminating groups contain at least one recurring unit having two biguanide groups of Formula (4):

Formula (4)

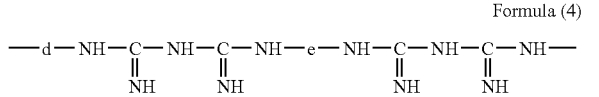

wherein d and e represent bridging groups which may be the same or different and in which together the total of the number of carbon atoms directly interposed between the pairs of nitrogen atoms linked by d plus the number of carbon atoms directly interposed between the pairs of nitrogen atoms linked by e is more than 9 and less than 17; and (ii) an acidic co-polymer of the Formula (1)

Formula (1)

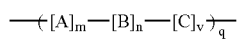

wherein:

[A] is of Formula (9),

Formula (9)

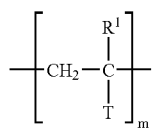

[B] is of Formula (10),

Formula (10)

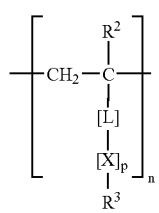

L in [B] comprises a group of the Formula:

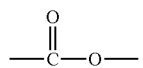

[C] is of Formula (12),

Formula (12)

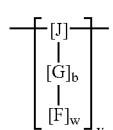

[G] in [C] is of the Formula:

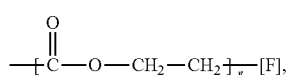

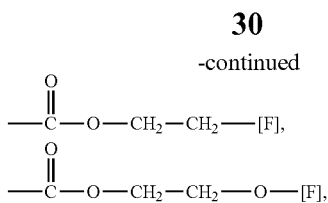

wherein d' is 2, 3, 4 or 5;
wherein:
[X] is of Formula (11),

Formula (11)

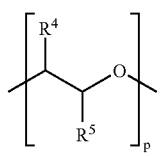

wherein [A], [B] and [C] may occur in any order;

T is a group of the Formula —C(O)OR$^6$, wherein R$^6$ is $C_{1-10}$-alkyl;

L and G each independently is an optionally substituted linking group;

R$^1$, R$^2$ and R$^3$ are each independently H, $C_{1-20}$-alkyl or $C_{3-20}$-cycloalkyl;

R$^4$ and R$^5$ are each independently H or $C_{1-4}$-alkyl;

q is 15 to 1000;

p is 3 to 50;

J is an optionally substituted hydrocarbyl group;

F is an acidic substituent;

b is 0, 1, or 2;

m is 1 to 350;

n is 1 to 75;

v is 1 to 100; and w is 1 to 4;

provided that at least one of R$^4$ and R$^5$ is H and provided that R$^1$, R$^2$, R$^3$, T, L, J and G do not contain a basic group; and wherein the pka value of the acidic substituent F on the monomer from which [C] is derived is less than 5.5 and wherein acidic substituent [F] comprises a carboxylic acid, a sulphonic acid, a phosphonic acid, or a phosphoric acid.

2. The composition of claim 1 wherein the polymeric biguanide is of Formula (6):

Formula (6)

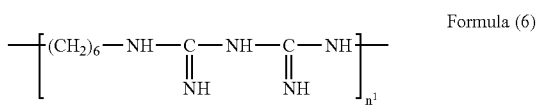

wherein n$^1$ is from 4 to 20.

3. The composition of claim 1 wherein the acidic co-polymer comprises a cloud point of greater than 15° C.

4. The composition of claim 1 wherein R$^1$, R$^2$ and R$^3$ are each independently H or —CH$_3$.

5. The composition of claim 1 wherein R$^4$ and R$^5$ are each independently H.

6. The composition according to claim 1 wherein [J] in [C] is of the Formula:

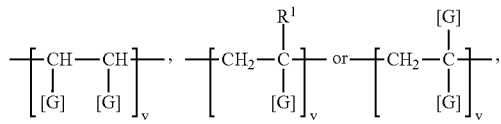

wherein $R^1$, v and [G] are as defined in claim 1.

7. A composition comprising
(i) an anti-microbial agent comprising a polymeric biguanide wherein the polymeric biguanide is a linear polymeric biguanide comprising a mixture of polymer chains in which the individual polymer chains excluding the terminating groups contain at least one recurring unit having two biguanide groups of Formula (4):

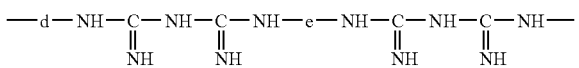

Formula (4)

wherein d and e represent bridging groups which may be the same or different and in which together the total of the number of carbon atoms directly interposed between the pairs of nitrogen atoms linked by d plus the number of carbon atoms directly interposed between the pairs of nitrogen atoms linked by e is more than 9 and less than 17; and (ii) an acidic co-polymer of the Formula (1);

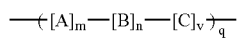

Formula (1)

wherein the acidic co-polymer of Formula (1) comprises [A] of Formula (13),

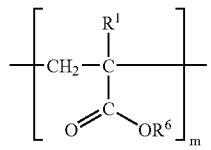

Formula (13)

[B] is of Formula (14), and

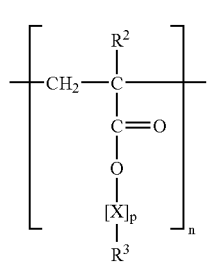

Formula (14)

[C] is of Formula (15),

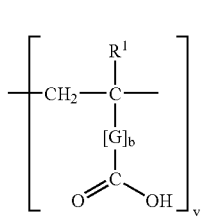

Formula (15)

[G] in [C] is of the Formula:

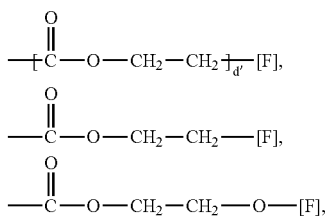

wherein d' is 2, 3, 4 or 5;
wherein:
[X] is of Formula (11),

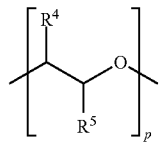

Formula (11)

wherein [A], [B] and [C] may occur in any order;
wherein:
G is an optionally substituted linking group;
$R^6$ is $C_{1-10}$-alkyl optionally substituted by a ketone, ether, —OH, epoxide, silane or ketoester group; and
$R^1$, $R^2$ and $R^3$ are each independently H, $C_{1-20}$-alkyl or $C_{3-20}$-cycloalkyl;
$R^4$ and $R^5$ are each independently H or $C_{1-4}$-alkyl;
q is 15 to 1000;
p is 3 to 50;
F is an acidic substituent;
b is 0, L or 2;
m is 1 to 350;
n is 1 to 75; and
v is 1 to 100;
provided that at least one of $R^4$ and $R^5$ is H and provided that $R^1$, $R^2$, $R^3$, and G do not contain a basic group; and
wherein acidic substituent [F] comprises a carboxylic acid, a sulphonic acid, a phosphonic acid, or a phosphoric acid.

8. The composition of claim 1 wherein the weight ratio of polymeric biguanide to acidic co-polymer is from 100:1 to 1:1000 weight percent.

9. The composition of claim 1 which comprises a pH of from 1 to 12.

10. The composition of claim 1 wherein the anti-microbial agent comprises a polymeric biguanide in combination with a fungicide.

11. A formulation comprising:
(i) a linear polymeric biguanide of claim 1; and
(ii) an acidic co-polymer of claim 1; and the formulation further comprising
(iii) a carrier.

12. The formulation of claim 11 wherein the carrier is water or a mixture of water and/or a water miscible organic solvent.

13. The formulation of claim 11 which comprises from 0.01 to 5% by weight polymeric biguanide and from 0.01 to 50% by weight acidic co-polymer.

14. The formulation of claim 11 which comprises a pH in the range of from 1 to 12.

15. A formulation comprising:
(i) a linear polymeric biguanide of claim 1 in combination with a fungicide; and
(ii) an acidic co-polymer of claim 1; and the formulation further comprising
(iii) a carrier.

* * * * *